United States Patent [19]

Siiman et al.

[11] Patent Number: 5,707,877
[45] Date of Patent: Jan. 13, 1998

[54] BIODEGRADABLE GELATIN-AMINODEXTRAN PARTICLE COATINGS OF AND PROCESSES FOR MAKING SAME

[75] Inventors: Olavi Siiman, Davie; Alexander Burshteyn, Hialeah; Ravinder K. Gupta, Pembroke Pines, all of Fla.

[73] Assignee: Coulter Corporation, Miami, Fla.

[21] Appl. No.: 493,973

[22] Filed: Jun. 23, 1995

Related U.S. Application Data

[60] Division of Ser. No. 968,158, Oct. 29, 1992, Pat. No. 5,466,609, which is a continuation-in-part of Ser. No. 607,253, Oct. 31, 1990, Pat. No. 5,169,754.

[51] Int. Cl.$^6$ ................................................ G01N 33/543
[52] U.S. Cl. ...................... 436/518; 436/528; 436/529; 536/51; 536/112
[58] Field of Search ...................... 536/112, 51; 436/518, 436/528, 529

[56] References Cited

U.S. PATENT DOCUMENTS

| | | | |
|---|---|---|---|
| 4,267,234 | 5/1981 | Rembaum | 436/526 |
| 4,452,773 | 6/1984 | Molday | 436/526 |
| 4,454,234 | 6/1984 | Czerlinski | 436/526 |
| 4,554,088 | 11/1985 | Whitehead et al. | 436/526 |
| 4,672,040 | 6/1987 | Josephson | 436/525 |
| 4,695,392 | 9/1987 | Whitehead et al. | 436/526 |
| 4,695,393 | 9/1987 | Whitehead et al. | 436/526 |
| 4,783,336 | 11/1988 | Margel et al. | 436/501 |
| 4,795,698 | 1/1989 | Owen et al. | 436/526 |

*Primary Examiner*—Christopher L. Chin
*Attorney, Agent, or Firm*—Michelle A. Kaye

[57] ABSTRACT

The invention relates generally to colloidal particle having a core material and a gelatin/aminodextran coating with pendent functional groups attached thereto. Biological substances or molecules, especially monoclonal antibodies, may be attached to said particles. The monoclonal antibody containing particles are useful in a variety of positive and negative biological assays.

13 Claims, 5 Drawing Sheets

BIODEGRADABLE GELATIN-AMINODEXTRAN PARTICLE COATINGS OF AND PROCESSES FOR MAKING SAME

RELATED INVENTION

This application is a division of application Ser. No. 07/968, 158, filed Oct. 29, 1992, now U.S. Pat. No. 5,466,609, issued Nov. 14, 1995, which is a continuation-in-part of application Ser. No. 07/607,253, filed Oct. 31, 1990, now U.S. Pat. No. 5,169,754, issued Dec. 8, 1992. This application also is related to application Ser. No. 07/827,347, filed Jan. 29, 1992, entitled FORMATION OF COLLOIDAL METAL DISPERSIONS USING AMINODEXTRANS AS REDUCTANTS AND PROTECTIVE AGENTS, now U.S. Pat. No. 5,248,772, issued Sep. 28, 1993; and to application Ser. No. 07/532,434, filed Jun. 4, 1990, and entitled IN SITU USE OF GELATIN IN THE PREPARATION OF UNIFORM FERRITE PARTICLES, now U.S. Pat. No. 5,062,991, issued Nov. 5, 1991. The specifications of these copending applications and patent are incorporated herein by reference. This application and these copending applications and patent are owned by a common assignee.

FIELD OF THE INVENTION

This invention relates generally to colloidal sized particles having a crosslinked gelatin or aminodextran coating with pendent functional groups attached thereto. Specifically, this invention relates to colloidal particles having a crosslinked gelatin or aminodextran coating that is functionalized to bind a pendant protein such as an antibody, to the method of making such particles and to the use of such particles in biological assays.

BACKGROUND OF THE INVENTION

The use of polymeric particles and magnetic particles to bind a compound has long been known and used in industrial and laboratory procedures. For example, the Merrifield resins, crosslinked styrene-divinylbenzene spheroidal beads, were among the earliest and most widely used modern substrate particles. They were used in organic synthesis, for heterogenizing homogeneous catalysts and in biochemical reactions. Since the Merrifield resins were fairly large, they could easily be separated by filtration. In some fields, however, it is desirable to use colloidal sized particles because the material to be bound is scarce, expensive or is to be used in a procedure where larger particles are not desirable. This is particularly true in the biochemical field. When particles are of colloidal size, however, their separation from liquid medium by filtration can become lengthy and difficult. In particular, colloidal particles tend to coat the surface of the filter and slow the process. The use of magnetic particles, specifically magnetic particles having a polymeric coating, has found great utility because such particles can be magnetically gathered to one side of a reaction vessel and the bulk of the reaction medium simply decanted. (The word "particles" as used herein encompasses spheres, spheroids, beads and other shapes as well. These words are used interchangeably unless otherwise specified.) The use of coated magnetic particles has found a particular utility in biological applications, especially where antibodies are bound to the surface coating of the particles. The bound antibodies may then be used to capture a specific biological substance from a test sample containing numerous biological samples or to capture undesired species from the test sample, leaving the desired species in the sample.

The categories of coated magnetic particles, also known as magnetic spheres or beads, can be divided into four general classes.

1. Core-and-shell beads with a magnetic core and a hard shell coating of polymerized monomer or a silanizing agent. See U.S. Pat. No. 4,267,234 to Rembaum (polyglutaraldehyde shell around ferrofluid core particles); U.S. Pat. No. 4,454,234 to Czerlinski (suspension or emulsion polymerized coating around submicron magnetic particles); U.S. Pat. Nos. 4,554,088, 4,695,392 and 4,695,393 to Whitehead et al. (silanized magnetic oxide particles of polydisperse size and shape); U.S. Pat. No. 4,672,040 to Josephson (polysilane coated magnetic particles); U.S. Pat. No. 4,783,336 to Margel et al. (suspension polymerized polyacrolein around ferrofluid particles); U.S. Pat. No. 4,795,698 to Owen et al. (bovine serum albumin coating); and U.S. Pat. No. 4,964,007 to yudelson (gelatin-gum arabic-surfactant coating);

2. Core-and-shell beads with a magnetic core and a loose shell of random coil or globular polymer which may or may not be crosslinked. See U.S. Pat. No. 4,452,773 to Molday (dextran coating around ferrofluid particles) and U.S. Pat. No. 4,795,698 to Owen et al. (protein such as bovine serum albumin around ferrofluid particles.

3. Magnetic latex materials formed by uniformly embedding ferrofluid particles in polystyrene latex particles. See U.S. Pat. No. 4,358,388 to Daniel et al.

4. Porous polymer particles filled with magnetic materials such as polymer-ferrite or polymer maghemite composite systems. See K. Nustad et al. "Monodisperse Polymer Particles In Immunoassays And Cell Separation", Microspheres: Medical and Biological Applications, A. Rembaum and Z. Tökès, eds. (Boca Raton, Fla.: CRC Press, 1988) pages 53–75; C.D. Platsoucas et al., "The Use of Magnetic Monosized Polymer Particles For The Removal Of T Cells From Human Bone Marrow Cell Suspensions", ibid. at pages 89–99; and U.S. Pat. Nos. 4,563,510, 4,530,956 and 4,654,267 [International Patent Publication No. WO 83/03920] to Ughelstad et al. (polymer coated magnetic particles prepared by treating compact or porous particles with a solution of iron salts and the use of such particles for medical, diagnostic or other purposes).

The usefulness of most polymer coated magnetic beads in medical and biological applications has been limited by practical considerations such as the uniformity of particle size and shape, the need for the biological reagent to be strongly bound to the particle, a preference for hydrophilic polymer coatings as opposed to hydrophobic coatings, and whether or not the coating is biodegradable. While biodegradability is of particular importance where a biological reagent is to be administered in vivo, it is also important in various cell sorting, separation and assay procedures. The most desirable coated magnetic particles would have the following features.

1. The particles should be as small as possible in order to maximize the surface area on which the biological reagent is coated, but the particles should still be easily separable with a small magnet. Small size and large surface area are desirable in order to use the least possible quantity of particles to remove the targeted substance; e.g., to interact with on the order of $10^6$ cells per sample in one step, thereby avoiding sequential additions and work-ups.

2. There should be a low non-specific binding of the antibody-coated particles to cell surfaces. The particle surface should be hydrophilic or covered with a coating of a hydrophilic substance to which the antibody is attached.

3. The polymer and antibody layers on the particles should be covalently bound to each other in order to reduce dissociation and conformational changes.

4. The coating on the magnetic particles and any molecular chains which link an antibody to the polymer surface should be metabolizable.

5. In positive selection of cells, a mechanism for quickly and easily recovering viable cells from the magnetic particles should be available in order that recovered cells can be cultured.

6. In the negative selection of cells, the antibody-coated particles should be sterile so that the remaining cells can be cultured.

7. For magnetic separation and sorting of cells and other biological substances, the preferred magnetic particles are "soft" magnetic particles. That is, particles which can be easily magnetized and demagnetized as opposed to hard or permanent magnetic. The particles can be ferromagnetic, ferrimagnetic or superparamagnetic. Ferromagnetic and ferrimagnetic particles are not limited in size, whereas superparamagnetic particles are limited to single domain structures of dimensions usually less than about 40 nanometers. (C. Kittel et al., Solid State Physics 3:437–464 (1956).

Problems exist with using each of the magnetic-composite particles from each of the above class in cell separation procedures. Some examples of the problems encountered are:

1. Ferrofluid core and the usual polymer outer shell particles have too small a magnetic moment to make them practical for use in cell separations where hand-held permanent magnets are used to collect and separate the magnetic particles. Such particles require the use high-field separation techniques which severely limits the volume of material which can be processed, thus limiting scale-up.

2. Ferrofluid-polystyrene particles prepared by emulsion polymerization cannot be tightly controlled in size and range from about 0.1 to 4 µm in diameter. Consequently, in cell separations using antibodies conjugated to such beads, the very small, kinetically-mobile magnetic particles which inherently possess the least magnetic moment tend to preferentially occupy the antigenic sates on a cell surface. As a result, the resulting cell-bead conjugates do not have a sufficient not magnetic moment to permit easy separation.

The use of magnetic particles having first and second layers of types B and A gelatin, respectively, and prepared as taught herein and in the copending priority application Ser. No. 07/607,253, overcomes these difficulties. However, gelatin coated particles have been found to have some problems regarding non-specific interactions with certain cells, notably platelets and phagocyte cells such as monocytes. The problem arises because the amino acid sequence of gelatin (as exemplified by the α-1 chain of rat and calf skin collagen) includes three regions with the tripeptide sequence Arg-Gly-Asp (RGD) which duplicates the RGD binding sequence of fibronectin, a component of the extracellular matrix that specifically promotes cellular adhesion. Those biological cells with fibronectin expressed on their surface have a specific affinity for collagen, which is equivalent to crosslinked gelatin. For example, antibody containing gelatin coated magnetic ferrite particles used in the separation of subsets of white blood cells will also bind to fibronectin on the surface of platelets and monocytes. The result is non-specific depletion of cells because monocytes and platelets are bound to the particles as well as those cells which bear antibody-specific antigens. The non-specific depletion of cells can be avoided through the use of an aminodextran as the outermost coating layer on coated particles. The use of dextran derivatives as carriers has been discussed by U. Manabe et el., J. Lab. Clin. Med. 104:445–454 (1984) (antibody-polyaldehyde dextran-methotrexate); L. B. Shin et al., Intl. J. Cancer 41:832–839 (1988) (antibody-aminodextran-methotrexate); A. R. Oseroff et al., Proc. Natl. Acad. Sci. USA 83:8744–8748 (1986) (antibody-aminodextran-chlorine 6); S. Rakestraw et al., Proc, Natl., Acad. Sci. USA 87:4217–4221 (1990) (antibody-dextran hydrazide-Sn(IV) chlorine 6); R. J. Mrsnay et al., Eur. J. Cell. Biol. 45: 200–208 (1987) (ouabain-aminodextran-gold particle); J. W. M. Bulte et al., Magnetic Res. 25:148–157 (1992) (anti particle); and other as described in S.S. Wong, "Chemistry of Protein Conjugation and Cross-Linking" (CRC Press, Boca Raton, Fla. 1991).

The various particles described above have been used in the biological arts to immobilize a variety of biological substances, particularly antibodies. In using such particles, immobilization of antibodies by covalent coupling is preferred to immobilization by antibody adsorption which requires careful and separate adjustment of pH and antibody concentration for each monoclonal antibody used. P. Bagchi et al., J. Colloid Interface Sci., 83:460–478 (1981); J. Lyklema, Colloids and Surfaces, 10:33–42 (1984); M. D. Bale et al., J. Colloid Interface Sci., 125:516–525 (1988); C. C. Ho et al., ibid., 121:564–570 (1988); "Proteins at Interfaces: Physicochemical and Biochemical Studies", ACS Symposium Series, No. 343, J. L. Brash and T. A. Horbett, Eds. (Washington: Amer. Chem. Soc., 1987); W. Norde, Adv. Coll. Interface Sci., 25:267–340 (1986); A. V. Elgersma et al., Abstracts of the 198th Amer. Chem. Soc. Meeting, Miami Beach, Fla., Sep. 10–15, 1989, COLL 0131; and D. E. Brooks, Annenberg Center for Health Sciences and H. B. Wallis Research Facility at Eisenhower Latex Conference, Orlando, Fla., Dec. 4–5, 1989. However, even when the pH and antibody are carefully controlled, there is little assurance that the orientation of adsorbed antibody will be such that an active adsorbed antibody will result. Adsorbed antibodies also have long term storage problems arising from antibody desorption from the particles' surfaces. Furthermore, proteins, such as antibodies, tend to achieve maximum adsorption on hydrophobic surfaces at or near the pI of the protein. However, if electrostatic interactions between charge groups are important, then the adsorbing surface and the adsorbate should have net opposite charges. Covalent coupling methods, on the other hand, are not as sensitive to these conditions.

Covalent coupling methods have been used with particles of magnetite embedded in carboxy-modified latex subsequently coated with aminodextran [R. S. Molday et al. FEBS. Lett., 170:232–238 (1984)] and derivatized with a number of antibodies as described in copending application Ser. No. 07/255,743 which is incorporated herein by reference. If the antibody is of IgG isotype, the covalent coupling method assures that the linkage between the antibody and the particles occurs at the antibody Fc or hinge region, and not at the antibody's Fab region. If the antibody is of pentameric IgM isotype which has only Fab regions exposed, the coupling of one Fab region to the particle will still leave four Fab regions exposed and available for reaction.

This invention provides for the preparation of magnetic particles having a biodegradable coating to which can be attached pendent biological substances, such as monoclonal antibodies. The particles of the invention can be used in various cell separation and assay methodologies. Biodegradability in the coating used on the magnetic core material is important in cell separation technology. For example, antibodies may be conjugated to gelatin/aminodextran coated magnetic particles such as manganese ferrite particles. These particles would contain a coating and a manganese-iron oxide core, all of which are biodegradable. In a positive cell selection procedure using such particles, once the desired cell has been isolated from other cells, the particles and coating can be allowed to degrade in a manner such that the cells are kept viable and can be cultured for further use. Alternatively, the enzyme collagenase can be used first to release the core material (magnetic or latex) by digestion of the gelatin/aminodextran coating. The core material can then be removed from the cell suspension before culturing the cells. In the negative selection of cells with such biodegradable beads, the beads can be left in the cell suspension from which targeted cells were removed without compromising the viability of the remaining cells. For example, in bone marrow purging operations using biodegradable magnetic beads, there is less concern about leaving behind some beads in the purged marrow that is to be transplanted in a patient. Currently, synthetic polymer-magnetite particles prepared by Ughelstad et al, U.S. Pat. No. 4,654,267 (WO 83/03920), and conjugated with antibody are being used in bone marrow purging. The polymer is not biodegradable and imparts a hydrophobic surface to these beads. This hydrophobicity, which is not present in the gelatin/aminodextran coated particles of the claimed invention, is responsible for non-specific interactions between the beads and cells. As a result of this non-specific interaction, the selectivity is poor and more beads must be used to attain the desired level of treatment. The claimed invention avoids these problems.

SUMMARY OF THE INVENTION

The invention provides discrete colloidal particles having a solid core and coated with a first layer of a water soluble gelatin and a second layer of an aminodextran, said coating being crosslinked or fixed by the action of a chemical crosslinking agent and having a plurality of pendent functional groups. The pendent functional groups may be or have terminal aldehyde or carboxylate groups, amine groups, sulfhydryl groups or maleimidyl groups, and polyclonal or monoclonal antibodies. The core may be metallic particles formed in gelatin solution or preformed particles which are then coated with the gelatin.

The invention provides discrete colloidal particles having pendent biological functional groups such as polyclonel and monoclonal antibodies covalently attached to the crosslinked second aminodextran layer by means of a heterobifunctional crosslinking agent so as to enable advantageous use of said antibody functionalized particles in biological separations and assays. The heterobifunctional crosslinking agent acts as a bridging group between the biological substance or functional group and the crosslinked gelatin or aminodextran.

The invention provides a process for the preparation of discrete colloidal particles having a solid core coated with a biodegradable first layer of crosslinked gelatin and biodegradable second layer of an aminodextran having pendent functional groups. The process comprises coating a solid core material which has a hydrophobic surface with first gelatin layer and a second aminodextran layer, crosslinking the adsorbed outer coating and derivatizing the crosslinked coating to obtain a product having a desired reactive species covalently bound to said crosslinked coating surface. The invention further provides a method for the preparation of particle bound polyclonal and monoclonal antibodies.

The invention provides a process for the separation, either positive or negative, and analysis of biological substances comprising contacting a solution containing a biological substance with an antibody covalently bound to the surface of a crosslinked gelatin/aminodextran coated solid core particle, incubating the resultant mixture at a temperature and for a time sufficient to form a complex between said antibody and said substance, separating the particles from the solution and analyzing the particles or the solution for the presence and/or absence of the desired substance.

DETAILED DESCRIPTION OF THE INVENTION

Figure 1:
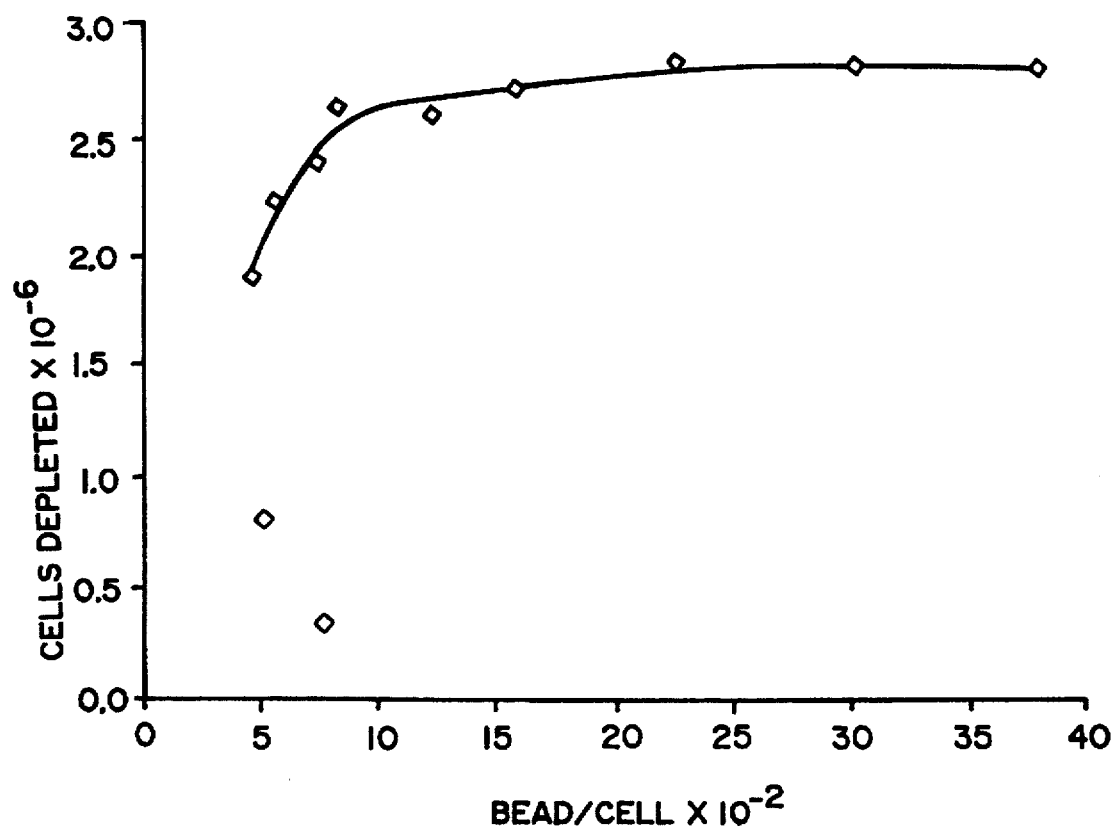
FIG. 1 shows the number of neutrophils depleted versus the magnetic bead-to-cell ratio.
Figure 2A:
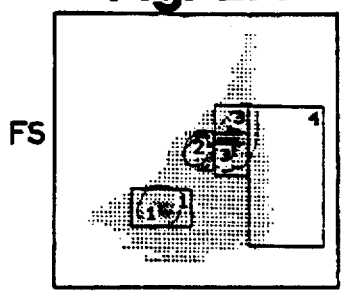
FIGS. 2A–2L show a distinct and progressive shift toward less forward scatter (FS) or smaller size and more side scatter (LSS) or greater granularity in the normal granulocyte region as higher titers of magnetic beads were added to cell samples.
Figure 2B:
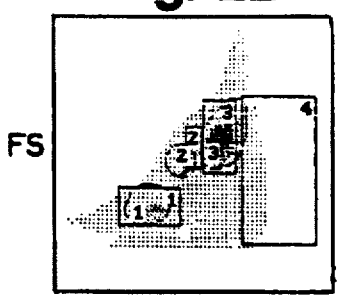
Figure 2C:
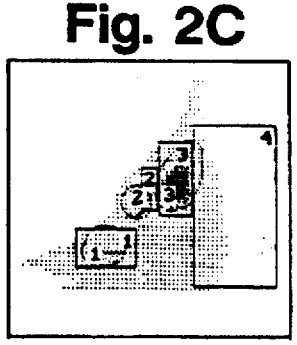
Figure 2D:
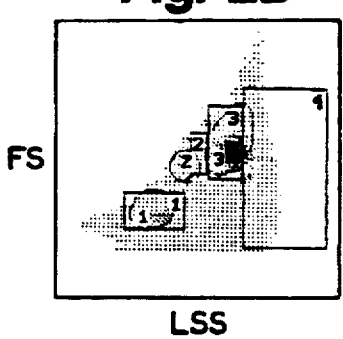
Figure 2E:
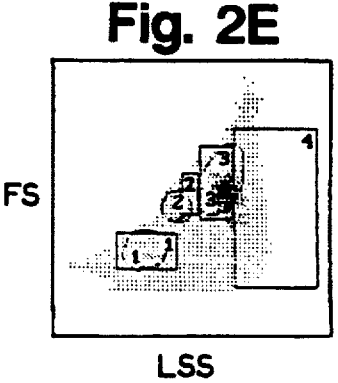
Figure 2F:
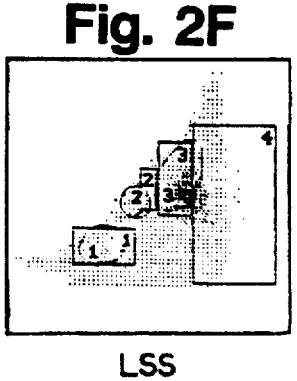
Figure 2G:
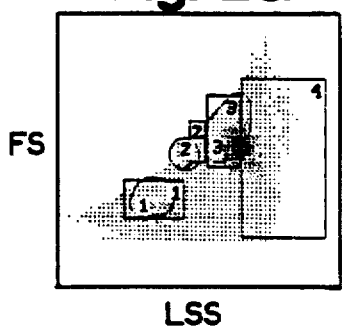
Figure 2H:
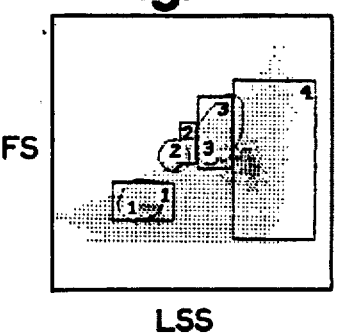
Figure 2I:
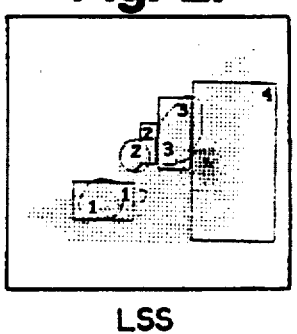
Figure 2J:
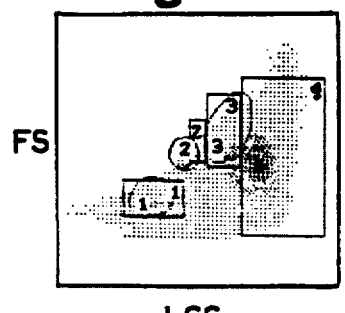
Figure 2K:
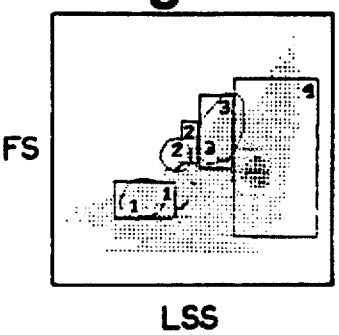
Figure 2L:
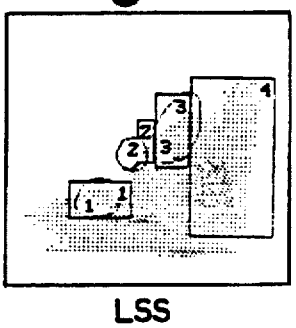

In the Detailed Description Of The Invention and Preferred Embodiments which follow, applicants place reactive maleimidyl groups on the crosslinked gelatin and/or aminodextran coated particles and reactive sulfhydryl groups on the antibodies. These may be reversed such that the maleimidyl groups are attached to the antibodies and the sulfhydryl groups are attached to the crosslinked gelatin and/or aminodextran. Applicants have also elected to use 2-iminothiolane hydrochloride as the model for the sulfhydryl reagent and sulfo-SMCC (described below) as the model for the maleimidyl reagent. Other reagents enumerated or of like nature and result may also be used.

Glossary of Biological Reagents

All of the monoclonal antibodies (Ab) referred to herein are identifying designations used by Coulter Corporation, Hialeah, Fla. for monoclonal antibodies made by Coulter Corporation. The following information further identifies the antibodies used herein. The use of these monoclonal antibodies is by way of example only and is not to be understood as limiting the invention. The term "CD" refers to "Cluster Designation" adopted by the International Workshops on Buman Leukocyte Differentiation Antigens. A.T.C.C. is the American Type Culture Collection, Rockville, Md.

| Antibody | CD | Description or Reference |
|---|---|---|
| T11 | CD2 | Derived from hybridization of mouse NS/1-AG4 cells with spleen cells of BALB/cJ mice immunized with T cell chronic lymphocytic leukemia cells. |
| T4 | CD4 | As T11, but immunized with peripheral human T lymphocytes. |
| T8 | CD8 | As T11, but immunized with human thymocytes. |

-continued

| Antibody | CD | Description or Reference |
|---|---|---|
| KC16 | — | U.S. Pat. No. 4,752,563; A.T.C.C. Deposit No. CRL 8994. |
| 1D3 | — | U.S. Pat. No. 4,931,395; A.T.C.C. Deposit No. HB 9445 |
| KC48 | — | U.S. Pat. No. 4,865,971; A.T.C.C. Deposit No. HB 9584 |
| MO2 | CD14 | R. F. Todd et al. J. Immunol., 126:1435 (1981). |
| PLT-1 | CD41 | R. F. Todd et al., Blood, 59:775 (1982); Griffith et al., Blood, 61:85 (1983). |
| KC56 | CD45 | Derived from hybridization of mouse Sp2/O-AG14 myeloma cells with spleen from BALB/c mice immunized with a derivative of the CEM cell line. |

Other reagents used herein and commercially obtainable from Coulter Corporation are:

MsIgG1-RD1/MsIgG1-FITC: Mouse IgG1-phycoerythrin [RD1]/ Mouse IgG1-Fluorescein Iso-thiocyanate [FITC].

T11-RD1/B4-FITC: Ab T11-phycoerythrin/Ab B4-FITC.

T4-RD1/T8-FITC: Ab T4-phycoerythrin/Ab T8-FITC.

1X PBS Dissolve 53.8 g $K_2HPO_4$ in 1.6 L distilled water. Add 12.8 g $KH_2PO_4$ and stir until dissolved. Then dissolve 340 g NaCl in the solution. After all salts dissolved, add distilled water to make up to 2 L volume and filter through a 0.2 μm filter. The resulting solution in 20X PBS. 1 X PBS is prepared by dilution of 1part 20X PBS with 19 parts distilled water. The 1X PBS solution has a pH in the range of 7.1–7.3, typically 7.2, a conductivity in the range of 13,500 to 15,500 μMho-$cm^{-1}$ and is 0.15M in NaCl.

Detailed Description

In using the method of the invention, uniform particles (the core material) in the size range of 0.1 to 5.0 microns are coated with gelatin or gelatin and aminodextran, and the coating is fixed by means of a chemical fixing 8 gent. The uncoated particles have a hydrophobic or partially hydrophobic surface. The preferred size of the particles is in the range of 0.1 to 1.0 microns.

The magnetic particles used in the claimed invention may be preformed magnetic particles that are dispersible in gelatin solution or they may be magnetic particles prepared by the in situ use of gelatin in the preparation of said magnetic particles. The in situ method for the preparation of monodispersed colloidal particles of ferrites of manganese, zinc, mixed manganese-zinc, iron, barium, cobalt and nickel involves the use of an aqueous metal hydrodroxide gel first formed by mixing ferrous and other metal salts in an aqueous gelatin solution with potassium or sodium hydroxide and potassium or sodium nitrate solution, all solutions being purged with nitrogen gas. The conversion of the gel to the metal oxide sol is achieved by mild thermal treatment at 90° C. (low temperature) for 4–72 hours, during which nitrate oxidation of ferrous iron occurs. The magnetic particles in the hydrosol are then washed and resuspended in a 1% aqueous solution of gelatin of the type described below or an aqueous aminodextran solution prior to further treatment as described herein. In preparing magnetic particles using in situ gelatin as described herein, only one type of gelatin has been found optimal for such use. This is type B or alkali-cured gelatin with a pI range of 4.75 to 5.0. The procedures for the preparation of magnetic particles using in situ gelatin are fully described in copending application Ser. No. 07/532,432, filed Jun. 4, 1990, the teachings of which is incorporated here by reference, and also described herein. The gelatins and aminodextrans which are crosslinked according to the present invention are given below.

Although ferrite particles can be prepared in situ in the presence of aminodextran as described in copending application Ser. No. 07/827,347, the interaction between the amino and the alcohol groups present on an aminodextran with the metal hydroxide and the resultant particles is weaker than the corresponding gelatin interaction. Consequently, ferrite particles are prepared in the presence of type B gelatin and preformed particles possessing a first layer of type B gelatin, as described in U.S. Pat. No. 5,062,991 and copending application Ser. No. 07/607,253, are suitable for use according to the present invention. Using such particles, e second layer of an aminodextran is coated on such particles in place of the second coating of type A gelatin described in copending application Ser. No. 07/607, 253. Particles of spinal ferrites such as $MnFeO_4$ and $ZnFeO_4$ which are ferrimagnetic are preferred over ferromagnetic ferrites such as magnetite ($FeFe_2O_4$), $CoFe_2O_4$ and $NiFeO_4$ because the net magnetization is considerably lower in the ferrimagnetic species due to partial cancellation of magnetic moment from two non-equal, sub-lattice magnetic structures. Consequently, ferrimagnetic species such as $MnFe_2O_4$ and $ZnFe_2O_4$, and their composite particles, in the 0.1 to 10.0 μm diameter size range possess less residual permanent magnetic dipole moments than magnetite particles in the same size range. This results in a lower tendency to form aggregates. Some aggregation tendency remains due to the trend to reduce the energy associated with large ratio of surface area to volume possessed by such small particles.

Gelatin is obtained from highly crosslinked collagen in fibrous tissue, such as skin or bone, which has been acid or base cured and then thermally degraded at or above 39° C. The collagen molecule combines the helical structure of the α-type proteins with the inter-chain hydrogen bonding of the β-type proteins. The three collagen peptide chains, each in the form of a left handed helix, are twisted about each other to form a superhelix. Upon treatment, the three peptide strands of the superhelix are separated by the breaking of inter-chain hydrogen bonds and replacing them with hydrogen bonds to water molecules. The separated peptides have random coil configurations. "The Theory of the Photographic Process", T. H. James,Ed., (New York: MacMillan Press, 1977). The α-1 peptide chain has been sequenced and found to have over 1000 residues. D. J. S. Hulmes et al., J. Mol. Biol., 79:137 (1973). They contain extensive segments of mainly non-polar residues; and the polar residues which are present are not localized into acidic or basic regions. Furthermore, in contrast to globular proteins which tend to expose their hydrophilic residues on their surfaces and bury their hydrophobtc residues within their structure {see R. E. Dickerson et al., "The Structure and Action of Proteins", (Menlo Park: Benjamin, 1969)}, random coil gelatin has exposed hydrophobic residues readily available for adsorption onto the surface of hydrophobic particles such as polystyrene latex particles or magnetite and ferrite particles. When aqueous gelatin is adsorbed onto the surface of s particle, its hydrophilic side chains (aspartyl, glutamyl and lysyl residues) tend to be directed externally to the aqueous medium. The lysyl groups, which function as the intramolecular crosslinkage points in collagen, will be accessible for cross linking in the adsorbed gelatin. Glutaraldehyde is frequently used as the crosslinking agent. U.S. Pat. No. 4,478,946 to Van Der Merwe et al. and S. B. Sato et al., a. Biochem., 100:1481–1492 (1986).

A number of different, usually bifunctional, crosslinking agents such as bis[2-(succinimido-oxycarbonyloxy)-ethyl] sulfone, disuccinimidytartarate, ethylene glycol bts (succinimidylsuccinate), disuccinimidyl suberate and glutaraldehyde may be used in the claimed invention. Glutaraldehyde, the preferred gelatin and/or aminodextran crosslinking agent, as commercially available, contains mainly monomer absorbing at 280 nm (nanometers). However, there is present in the commercial product a significant amount of polymeric material which gives rise to an absorbance at 235 nm. The polymeric species, probably trimers or linear oligomers, are of sufficient length to form intra- and inter-molecular bridges between amino groups present on the adsorbed gelatin. By judiciously selecting the reaction time between the adsorbed gelatin and/or aminodextran coating and glutaraldehyde, the gelatin and/or aminodextran coating can be suitably fixed on the core particles so that it will not be removed during subsequent separation, reaction and washing steps. Large flocs created by excessive crosslinking of free gelatin and/or aminodextran can thereby be avoided and interparticle crosslinking is negated.

Several types of gelatin are available for use in the present invention, such as type A, acid cured, isoelectric point pH 8.3–8.5 end type B, alkali cured, isoelectric point, pH 4.75–5.0. Each type is available in e variety of Bloom Numbers which indicate gel strength. Type A gelatin Bloom Numbers useful in the claimed invention range from 60 to 300. Type B Bloom Numbers useful in the claimed invention range from 60 to 225. The type A, 175 Bloom gelatin used in the preferred embodiment of particles having a second crosslinked gelatin layer is preferred and was selected for its relatively large number of lysyl residues and its lower Bloom number in order to minimize intermolecular interactions between gelatin molecules. For optimum adsorption on magnetite and ferrite particles, it was buffered to pH 8.4, the middle of its isoelectric point range, at which pH it is most soluble in water and gives the least viscous solution. The instability of gelatin adsorbed on ferrite particles, which instability arises when glutaraldehyde is added, was overcome by the present invention by the use of more dilute particle and gelatin concentrations [0.1% weight/volume (w/v) instead of the 2.5% w/v solids suspension that was used in other reactions herein in conjunction with an inert polymeric stabilizer, polyvinylpyrrolidone (PVP), that does not react with glutaraldehyde. The use of the stabilizer and the 25-fold lower gelatin concentrations avoids interparticle crosslinking during the glutaraldehyde fixation reaction. Since polymer desorption is a very slow process relative to the time of the glutaraldehyde fixation reaction approximately 6 minutes, a stable gelatin coating around the core particle was produced.

In order to be useful in the biological and medical arts, the fixed (crosslinked) gelatin only (2 layers) or gelatin/aminodextran coating should contain functional groups which can be conjugated with biologically active substances such as antibodies to produce immobilized biologically active substances attached to the particle surface. Covalent coupling of biological substances to the particle surface is preferred over simple adsorption. The coupling of an antibody, either polyclonal or monoclonal, to the crosslinked gelatin or aminodextran surface is accomplished by the use of "short chain" diamines or polyamines and a heterobifunctional reagent. (Hereafter, the word polyamine includes diamines). The polyamine is reacted with residual aldehyde or carboxylate groups, either naturally occurring or present by the steps of this invention, present on the crosslinked gelatin surface. The use of polyamine serves not only to block aldehyde/carboxylate groups, but also serves to replenish gelatin amino groups such as lysyl amino groups or aminodextran amine groups which were depleted during the crosslinking process. This procedure is generally accomplished in two steps. In the first step, unreacted terminal aldehyde groups of the crosslinking agent are reacted with a polyamine followed by sodium borohydride ($NaBH_4$) reduction of the resulting Schiff's base to create stable, saturated C—N linkages. In the second step, exposed carboxylic acid residues (glutamic, aspartic) of gelatin are coupled to polyamine in the presence of a water soluble carbodiimide such as 1-ethyl-3-(3-dimethylaminopropyl) carbodiimide (EDAC).

Short chain diamines or polyamines are preferred in order to avoid crosslinking neighboring aldehyde or carboxylic acid groups on the same particle or to avoid linking such groups on different particles. One polyamine amine group reacts with the crosslinked gelatin or aminodextran surface and the other(s) remains unreacted and available for coupling, directly or indirectly, to a biological substance. Examples of 'short chain' diamines or polyamines include ethylenediamine, phenylenediamine, propylenediamine, 1,4-cyclohexanediamine, cyclohexenediamine, tetramethylenediamine, diethylenetriamine, 1,5-diamino-3-(2-aminoethyl)pentane [$(H_2NCH_2CH_2)_3C$] and other polyamines of general formulas $H_2NCH_2—(CH_2)_x—CH_y(CH_3)_z—NH_2$ and $C_6H_{4+a}(NH_2)_{21}$ where x=0–3, y=1 or 2 and z=1 when y=1 or z=0 when y=2, and a=0 or 6. Ethylenediamine is preferred. Aminodextrans may also be used as a preferred polyamine reagents.

The coupling of the biological substance to the particle involves activation of the free amino groups of the coated, crosslinked particles with a water soluble heterobifunctional reagent such as 2-iminothiolane hydrochloride (IT), sulfosuccinimidyl4-(N-maleimidomethyl) cyclohexane-1-carboxylate (sulfo-SMCC), m-maleimidobenzoyl-N-hydroxysuccinimide ester, N-succinimidyl-3-(2-pyridyldithio)propionate, succinimidyl-4-(p-maleimidophenyl)butyrate, N-succinimidyl-(4-iodoacetyl) aminobenzoate, the reagents listed above as substitutes for glutaraldehyde and the like. The 2-iminothiolane hydrochloride and the maleimidyl/succinimidyl reagents are preferred. E.Ishikawa, Immunoassay Supp., 1:1–16 (1980) and J. Immunoassay, 4:209–227 (1983); M. Imagawa et al., J. Appl. Biochem., 4:41–57 (1982); and M. D. Partis, J. Protein Chem., 2:263–277 (1983). When using sulfo-SMCC, the active sulfosuccinimidyl ester end of sulfo-SMCC will react at pH 7.0–7.5 with amines to give peptide bonds. The sulfo-SMCC/diamine bridging unit which results is approximately 16 Angstroms in length.

When performing the polyamine and sulfo-SMCC reactions, particle aggregation was monitored by microscopic examination (1000× magnification) and by light scattering analysis using a Coulter N4MD submicron particle size analyzer (Coulter Corporation, Hialeah, Fla.), or similar instrument.

The maleimidyl group of sulfo-SMCC will react at pH 6.5–7.5 with free sulfhydryl groups to form a stable, covalent thioether bond. However, it is essential that the coated particles with which sulfo-SMCC is reacted contain no free sulfhydryl groups which could react with the maleimidyl end of sulfo-SMCC. Sulfhydryl groups are found on or generated from cystine and cysteine amino acid residues of which gelatin or aminodextran have very few or none. Consequently, the crosslinked particles of the claimed invention do not require a protein modifier to block free sulfhydryl groups prior to reaction with sulfo-SMCC.

Biological substances, particularly either monoclonal or polyclonal antibodies, can be covalently linked to the maleimidyl end of sulfo-SMCC functionalized particles by means of sulfhydryl groups present, either naturally or by derivatization, on said biological substances. Biological substances which have cysteinyl residues inherently contain sulfhydryl groups. To introduce additional sulfhydryl groups, the biological substances' amine groups are activated with Traut's reagent, 2-iminothiolane hydrochloride (IT), at a pH in the range of 7–10. M. Erecinska, Biochem. Biophys. Res. Commun., 76:495–500 (1977); J. M. Lambert et al., Biochemistry, 17:5406–5416 (1978); and M. E. Birnbaumer et al., Biochem J., 181:201–213 (1979). When the bio-substances are antibodies, antibody lysyl and terminal amine groups are activated by IT. In the present invention, reaction conditions and the concentration of reactants were varied to determine the optimal coupling so that the biosubstance, especially antibody, when conjugated with the substrate particles, retains its maximum functional activity. Although maleimides react quite rapidly with sulfhydryl groups in solution, the same groups immobilized on particles were given longer reaction periods to react with protein. Particle and antibody concentrations during antibody conjugation were optimized to avoid aggregation, particularly when IgM antibodies were used. The procedures optimized for IgM antibodies can be used for all monoclonal antibodies with an isoelectric point range of about 5.0 to about 9.0. Generally, about 30-fold less antibody was required to achieve covalent coupling than is required for simple adsorption; a consequence of importance where expensive or hard to obtain antibodies are involved.

The optimum concentration of iminothiolane-activated antibody to use in conjugation reactions with maleimidyl-activated particles was determined by the use of activated antibody binding curves (Surface Antibody vs Total Antibody Concentration). After a typical conjugation period, a sample is taken and filtered through a 0.2 μm low-protein binding filter. The filtrate is analyzed spectrophotometrically and the surface antibody is determined by the difference between the total antibody in the starting solution and the antibody in the filtrate (Total Antibody-Filtrate Antibody). The binding data in antibody (Ab) concentration dependent runs show Langmuir isotherm-type characteristics; i.e., a linear low concentration region for total antibody versus surface antibody concentration, a smooth inflection point and a plateau indicating saturation at the particle surface at high concentrations. The antibody concentrations actually used were those at the inflection point or at concentrations slightly above the inflection point. Binding constants were obtained graphically by recasting the equation of a hyperbole into one for a straight line. A double reciprocal plot of $1/n_2^s$ versus $1/C_2$ was constructed, where $n_2^s$ is the number of moles of IT-Ab bound per gram of particles and $C_2$ is the molar concentration of free IT-Ab at equilibrium. Linear plots are indicative of Langmuir-type binding behavior. The binding constants $K_1 = n^s K$ of IT-Ab for sulfo-SMCC-activated ferrite particles were calculated using the equation $1/n_2^s = 1/(n^s K C_2) + 1/n^s$, where $K$ is the intrinsic binding constant and $n^s$ is the number of moles of binding sites per gram of ferrite particles. Linear regression analysis of plots for various monoclonal antibodies gave the following results:

| Ab T11: | $K = 1.3 \times 10^6 \, M^{-1}$ | $n^s = 5.9 \times 10^{-8}$ mol/g |
| Ab KC16: | $K = 6.4 \times 10^6 \, M^{-1}$ | $n^s = 5.1 \times 10^{-7}$ mol/g |
| Ab 1D3: | $K = 2.7 \times 10^6 \, M^{-1}$ | $n^s = 2.0 \times 10^{-7}$ mol/g |
| Ab MO2: | $K = 1.8 \times 10^7 \, M^{-1}$ | $n^s = 7.1 \times 10^{-7}$ mol/g |

The results for the ferrite particles compare favorably with similar data for commercially available carboxy-modified latex beads (23% magnetite, 0.980 μm dis., obtained from Rhone-Poulenc) covalently coated with aminodextran and conjugated to monoclonal antibodies end protein. These results are:

| Ab T11: | $K = 6.5 \times 10^5 \, M^{-1}$ | $n^s = 1.1 \times 10^{-7}$ mol/g |
| Ab KC16: | $K = 3.2 \times 10^6 \, M^{-1}$ | $n^s = 6.9 \times 10^{-8}$ mol/g |
| Ab 1D3: | $K = 3.2 \times 10^5 \, M^{-1}$ | $n^s = 1.7 \times 10^{-7}$ mol/g |
| Ab MO2: | $K = 2.0 \times 10^6 \, M^{-1}$ | $n^s = 1.6 \times 10^{-7}$ mol/g |
| Ab KC48: | $K = 2.5 \times 10^5 \, M^{-1}$ | $n^s = 7.6 \times 10^{-8}$ mol/g |
| Ab PLT-1: | $K = 2.8 \times 10^5 \, M^{-1}$ | $n^s = 2.2 \times 10^{-7}$ mol/g |
| Streptavidin: | $K = 1.3 \times 10^6 \, M^{-1}$ | $n^s = 9.5 \times 10^{-8}$ mol/g |

DESCRIPTION OF THE PREFERRED EMBODIMENTS USING IN SITU FORMED AND PREFORMED MAGNETIC PARTICLES

I. Preparation of Magnetic Particles Having First and Second Gelatin Layers

Preparation of Magnetite and Other Magnetic Particles in Gelatin Solution.

10 mmol (5 ml) of 2M $KNO_3$ solution, 12.5 mmol (2.5 ml) of 5M KOH solution and 11.25 ml of double distilled water (DDW) were mixed and purged with $N_2$ gas for 10 minutes (Solution A). 6.25 mmol (6.25 ml) of 1M $FeSO_4$ solution and 25 ml of freshly prepared, $N_2$ purged, 2% type B, 225 Bloom, bovine skin gelatin solution [useful gelatin solution range is from about 0.8% to about 2.0%] were then added to Solution A in a Pyrex® bottle, mixed, swept with $N_2$ gas, capped tightly, and placed undisturbed in an oven at 90° C. for 4 hours. After the suspension of black magnetite particles had reached room temperature, they were sonicated for ½ hour, washed with 1% type B, 225 Bloom gelatin solution, and then contacted with a large excess of 1% w/v gelatin as is the next step.

Metal ferrites may also be prepared using gelatin in situ in their preparation. In trials with other metals, namely $Mn^{2+}$, $Zn^{2+}$, $Co^{2+}$, $Ni^{2+}$, and $(M^{2+})$, the molar ratio of $M^{2+}:Fe^{2+}$ was kept at 1:2, but nitrate was used instead of sulfate for $Co^{2+}$ and $Ni^{2+}$. The total metal-to-hydroxide molar ratio was maintained at 1:2; but the relative $KNO_3$ to total metal and $KNO_3$ to KOH molar ratios were altered. preparing the mixed Mn/Zn ferrite, a 1:1 molar ratio of manganese sulfate to zinc sulfate and the same total molar amount of non-ferrous metal ions were used. The following is an example.

10 mmol (5 ml) of 2M $KNO_3$ solution, 18.75 mmol (3.75 ml) of 5M KOH solution and 6.875 ml DDW were mixed and purged with $N_2$ gas for 10 minutes (Solution C). 6.25 mmol (6.25 ml) 1M $FeSO_4$ solution, 3.125 mmol (3.125 ml) of 1M $Co(NO_3)$ solution and 25 ml of type B, 225 Bloom, bovine skin gelatin solution were mixed end purged with $N_2$ gas for 10 minutes. (Solution D). Solution D was added to Solution C in a Pyrex® bottle, mixed, swept with $N_2$ gas, capped tightly, and placed undisturbed in an oven at 90° C. for 5 hours. After the suspension of brown particles had reached room temperature, it was sonicated for ½ hour, the particles washed with 1% type B, 225 Bloom gelatin solution and then contacted with a large excess of 1% w/v gelatin as in the next step.

Using the methods described above, cobalt and nickel ferrite particles of about 0.1 and 0.2 μm in diameter and of spherical shape were formed in large, loosely-held brown aggregates. Zinc gave low yields of light brown magnetic material of less than 0.2 μm diameter even after 72 hours of heat treatment. Dark brown manganese ferrite particles of uniform, spherical shape and 0.3 μm diameter were obtained as single particles in 83–88% yields. Similar light brown manganese-zinc ferrite particles were produced in 49–55% yield after 72 hours of heat treatment at 90° C. For barium, the procedure was modified since $BaSO_4$ is insoluble in water. (Except for the case where barium is present, the divalent metals may be used as their chlorides or sulfates as well as their nitrates). Thus 6.25 mmol (6.25 ml) of 1M $FeCl_2$ solution, 0.5 mmol (5.0 ml) of 0.1 $Ba(NO_3)_2$ solution and 25 ml of 2% gelatin were mixed and purged with $N_2$ gas for 10 minutes (Solution D). Solution C and the remainder of the ferrite preparation procedure was unchanged except 10 mmol KOH solution (2 ml) was used and the heat treatment was continued for 20 hours. Black barium ferrite particles of uniform non-spherical shape with a 0.2 μm diameter were produced.

Preparation of Gelatin Coated Magnetic Particles.

A quantity of magnetic particles, for example, manganese ferrite particles, of uniform size (0.3 μm) and spherical shape and prepared using in situ gelatin according to the procedures described above were contacted with a large excess of 1% w/v, type B, 225 Bloom aqueous gelatin solution. Alternately, preformed (i.e., formed by methods other than the in situ use of gelatin), dispersible magnetic particles, for example, manganese ferrite particles, of uniform size (0.3 μm) and spherical shape were contacted with a large excess of 1% w/v, type B, 225 Bloom gelatin solution at ambient temperature for approximately 60 minutes. The particles (either of the above) were then magnetically separated and washed five times with a 2% w/v, type A, 175 Bloom gelatin solution in 0.2M aqueous sodium chloride, pH 8.4. After washing, the particles were stored at ambient temperatures for up to several months as 2.5% w/v (weight/volume) solids suspension in a 2% w/v aqueous solution of the type A gelatin containing 0.2M sodium chloride, 0.1% w/v sodium azide at pH 8.4. Provided the azide content of the storage solution is maintained, the suspension can be stored for up to about 3 months.

Crosslinking the Adsorbed Gelatin.

62.5 μL of 25% aqueous glutaraldehyde (0.156 mmol) solution were added to 120 ml of 1% aqueous polyvinylpyrrolidone (MW:=40,000) in 0.2M aqueous sodium chloride, pH 7.2. To this, 5 ml of the 2.5% solid suspension prepared above were added to the glutaraldehyde solution and the resulting suspension was mixed at ambient temperature for a time in the range of 3–15 minutes, preferably about 6 minutes.

Blocking of Unreacted Aldehyde Groups.

0.105 ml of 99% ethylenediamine (1.56 mmol) was added to a 125 ml suspension of the fixed, gelatin coated magnetic particles (0.1%w/v solids) in 1% PVP solution, 0.2M in sodium chloride, pH 7.2. The resulting suspension was mixed for a time in the range of about 1 to 4 hours, preferably about 2 hours, in a 250 ml tissue culture flask. At the end of the mixing time, 1.25 ml of a 10 mg/ml solution of sodium borohydride ($NaBH_4$) in 0.1 mM KOH were added to the magnetic particles end the resulting suspension was mixed for an additional 15 minutes. The particles were then magnetically separated and washed a plurality, preferably three, times with 0.2M aqueous sodium chloride.

Reaction with Fixed Gelatin's Carboxylate Residues.

2.11 ml of 99% ethylenediamine were added to an 118 ml suspension of the aldehyde-blocked beads, 0.1% w/v solids, in 0.2M aqueous NaCl. The resulting suspension was physically and sonically mixed for approximately 15 minutes. After this mixing, 4.5 ml of 10 mg/ml EDAC in 0.2M NaCl was added and the suspension was first physically and sonically mixed for approximately 15 minutes, and finally physically mixed for a time in the range of about 8–16 hours. The contents of the flask were then magnetically separated, washed a plurality of times with 1X PBS, sonically mixed in 1X PBS for approximately 30 minutes, and finally concentrated to 5 ml of 2.5% w/v solids in 1X PBS. For large scale (100×) preparations, the previous aldehyde blocking step and the EDAC coupling step have been combined to avoid multiple separations and washings. The combination of steps did not result in any loss of activity in the final antibody-conjugated beads.

Crosslinking the Adsorbed Gelatin Without Polyvinylpyrrolidone Stabilizer Present.

5 ml of 2.5% w/v solids manganese ferrite particles suspended in 2% w/v type A, 175 Bloom gelatin in 0.1M phosphate buffer, pH 8.4, which were prepared as described above were magnetically separated. The clear supernatant liquid was discarded and the residue of magnetic particles was resuspended in 5 ml of 3 mg/ml glutaraldehyde solution prepared by mixing 56 μL of 25% aqueous glutaraldehyde solution with 5 ml of 1 mM aqueous potassium hydroxide, pH 10.00. The resulting suspension of magnetic particles was mixed, preferably roller mixed, for about 30 minutes. After the glutaraldehyde addition and mixing was completed, about 34 μL of ethylenediamine (10:1 diamine-to-glutaraldehyde molar ratio) were added to the reaction mixture which was then stirred for an additional 2–3 hours. Subsequently, about 0.313 ml of a 40 mg/ml solution of sodium borohydride in 1 mM KOH was added to the reaction and the resulting mixture stirred for about 10–30 minutes. The crosslinked particles were then washed three times using magnetic separation and resuspended in 5 ml of 1 mM aqueous potassium hydroxide.

Activation of Diamine Treated Particles with Sulfo-SMCC.

In general, 27 μL of freshly prepared 10 mg/ml sulfo-SMCC in 1X PBS were used per milliliter of 2.5% w/v magnetic particle suspension. In a typical preparation, 135 μL of the sulfo-SMCC solution were added to 5 ml of 2.5% w/v particles. The mixture was then roller mixed in a 15 ml plastic centrifuge tube for approximately one hour, sonically mixed for approximately 5 minutes, magnetically separated, and washed a plurality of times with 1X PBS.

The functionalized, crosslinked, gelatin coated particles resulting from the above series of steps have pendent maleimidyl groups end are suitable for a variety of medical end/or biological uses. If the substance which is desired to be conjugated to the particles has a sufficiency of active sulfhydryl groups, activation of that substance is not necessary, and the following step may be skipped.

Antibody Activation with 2-iminothiolane Hydrochloride.

A 51.24 mg/ml concentrate of T11 monoclonal antibody in 1X PBS containing 0.1% $NaN_3$ was prepared. For 10 mg of T11 antibody and 15 mg/ml antibody concentration during coupling, the total reaction volume should be 0.667 ml. Using a 15:1::IT:T11 activation ratio, 0.9375 μmol (0.129 mg) IT (65 μL of 2mg/ml IT) in 1X PBS is required. Therefore, 0.407 ml of 1X PBS solution was added to 0.195 ml of T11 concentrate, to which resulting solution an additional 65 μL of 2mg/ml IT solution was added. The net resulting solution was roller mixed in s tube reactor for 1 hour. The content of the reaction tube was then applied to the top of a 20 ml G-0 Sephadex column, equilibrated and washed with 100 ml 1X PBS. The derivatized antibody was eluted using 1X PBS and e plurality of 2.5 ml fractions were collected with the aid of a UV monitor. Fractions in the middle of the band absorbing at 280 mm were pooled and the $A_{280}$ value was used to determine T11/=T antibody concentration. Typically, the T11/IT concentration was about 3.0 mg/ml. The T11/IT solution may be concentrated by solvent removal.

Conjugation of T11/IT with Sulfo-SMCC Derivatized Particles.

In a laboratory scale conjugation, total volume 5 ml, the concentration of particles was 2.5% w/v solids and the T11/IT concentration was 0.9 mg/ml. In one sample, when the purified T11/IT solution concentration was 1.850 mg/ml, then 2.392 ml of T11/IT antibody solution in 1X PBS was added to 5 ml of 2.5% w/v solids sulfo-SMCC activated particles which had been preconcentrated by the removal of 2.432 ml of supernatant. The T11/IT solution was added to the particles in 0.5 ml increments with sonic and rapid physical mixing between additions. The resultant solution was then roller mixed in a 15 ml tube for approximately two hours. A 1 ml test sample was then taken, filtered through a low-protein binding 0.2 µm filter, and the filtrate analyzed spectrophotometrically for T11 antibody by measuring the absorbance at 280 nm; $A_{280}$=c (supernatant)=0.3986 mg/ml. [Measurement by difference, c (surface)=c (total)−c (supernatant)]. Thus c (surface)=0.9 mg/ml−0.3986 mg/ml= 0.501 mg/ml. This translates to a T11 surface loading of 20 mg T11 per gram particles or, for a specific surface area of 4.89 $m^2$/g for manganese ferrite particles, a 4.1 mg T11/$m^2$ particle surface area. Similar procedures with 2-and 3-fold dilutions of particle concentration, but the same total antibody concentration during conjugation, gave higher surface antibody loading. However, a limitation was reached when a 4-fold dilution of the particles concentration did not yield higher surface coverage of antibody.

Blocking Unreacted Maleimidyl and Sulfhydryl Groups.

Unreacted maleimidyl groups on the sulfo-SMCC activated particles were blocked with L-cysteine after antibody conjugation. Typically, 0.480 ml of 5 mg/ml L-cysteine in 1X PBS was added to remaining 4 ml of the conjugation mixture of the previous step and the resulting solution was roller mixed for 15 minutes. Unreacted sulfhydryl groups were blocked by the addition of 0.534 ml of 20 mg/ml iodoacetamide in 1X PBS followed by the addition of 0.100 ml of 1M, pH 9.8 sodium borate buffer solution. The resulting solution was roller mixed for 30 minutes, the blocked conjugation mixture was magnetically separated and the particles washed three times with 1X PBS containing 1% bovine serum albumin (fraction V, heat shock) and 0.1% $NaN_3$ (BSA buffer solution). After washing, 4 ml of the foregoing BSA solution were added to the particles, the particles roller mixed for approximately 1hour, stored at 4° C. for a time in the range of about 8–16 hours, magnetically separated and washed three additional times with BSA buffer.

Antibody containing particles prepared according to the method described herein have been found useful in various cell separation assays. The biological substances used in assays utilizing the Invention may be selected from the groups consisting of normal or non-normal T-cells, B-cells, leukocytes, viruses, erythrocytes, cells of the breast, uterus, colon, kidney, liver, lung, testes, stomach, thyroid and parathyroid, and the like; provided that the biological substance contains an antigenic determinant capable of binding to an antibody.

In an embodiment of the invention equivalent to the magnetic particle embodiment described above, the maleimidyl groups and the sulfhydryl groups are transposed. That is, the crosslinked gelatin coated particles are derivatized to have pendent groups ending in reactive sulfhydryl groups in place of the maleimidyl groups described above and the antibodies are derivatized to have reactive maleimidyl groups in place of the sulfhydryl groups described above. The methods used to prepare this equivalent embodiment are the same as described above. In both cases, the antibody is connected to the gelatin surface by a molecular bridge prepared as described.

The following examples are given to illustrate the utility of the claimed invention and are not to be taken as limiting said invention.

EXAMPLE 1

Protocol for Magnetic Bead Depletion of T-cell and B- cell Populations.

Mononuclear cells (MNC) were obtained from whole blood samples by density isolation on Ficoll-hypaque gradients and washed with 1X PBS. $1\times10^6$ MNC in 1 ml 1X PBS were added to a series of tubes containing 5, 10, 25, 50 and 100 µL of the monoclonal antibody (mAb) conjugated magnetic particle suspension (2.5% w/v) being tested. Two tubes were set up for each depletion and for the undepleted control. The resulting suspensions were then mutated for 3 minutes in a multi-tube vortexer or a single tube mutator. At the end of incubation, the cell suspension was placed for a total of 2 minutes in the magnetic field provided by a single tube magnetic rack. At the end of the magnetic separation, unbound cells were extracted by withdrawing all the clear liquid from the center of the tube with a Pasteur pipet.

For T- or B-cells (T11, T3, T4, T8, B1, B4), the cell suspension collected after depletion was compared directly to the original cell suspension prior to particle depletion. The samples, original and depleted, were centrifuged for 5 minutes et 1200 rpm end the supernatant decanted to leave approximately 100 µL of 1x PBS remaining in each tube. One tube of each pair of depletion tubes was then stained with 10 µL CYTO-STAT® MsIgG1-RD1/MsIgG1-FITC control reagent (MS) and the other tube was stained with 10 µL CYTO-STAT® T11-RD/B4-FITC reagent (for T11, T3, B1 or B4 depletions) or with 10 µL of T4-RD1/T8-FITC reagent (for T4 or T8 depletions) at room temperature for 10 minutes. At the end of incubation, 500 µL of 1X PBS were added to each sample and the samples were analyzed by flow cytometry. The samples were analyzed on the EPICS® Profile using the MBead 2-Color program. (EPICS® and CYTO-STAT® are registered trademarks of Coulter Corporation). As the original sample stained with Ms control reagent was being run, it was checked to determine whether the lymphocyte population was fully incorporated in Bitmap 1, and adjustments were made if necessary. The left side of discriminator 2 was set for each fluorescence histogram on the channel which would give <1% positive staining. This was done for each sample stained with Ms control reagent and then the corresponding tube stained with specific antibody was analyzed. The data were collected and recorded as the absolute number of positive staining cells in the red and green histograms (T and B or T4 and T8) not percent positive. Test results are summarized below.

EXAMPLE 2

Protocol for Magnetic Bead Depletion of Red Blood Cells (RBC).

100 µL of Na4EDTA-anticoagulated whole blood were placed in a series of reaction tubes. To each tube, 25 to 150

μL of KC-16 conjugated magnetic particles suspension (2.5% w/v) were added and the total volume was adjusted to 250 μL using 1X PBS. The suspension were nutated for 3–5 minutes in a multitube vortexer or a single tube nutator at low mixing speed. When nutation was completed, 1 ml of 1X PBS was added to each sample tube which was then placed on a magnetic rack for 2–5 minutes. All the supernatant was removed from each tube using a Pasteur piper and saved in labelled tubes. Samples were analyzed on a Coulter S-plus® IV or similar rbc counter as total rbc number/ml whole blood. The positive control was 100 μL whole blood plus 1,150 ml 1X PBS to give 100% rbc count and the negative control was 100 μL whole blood plus 1.150 ml of Batch lyse or similar lysing agent to give 0% rbc count. Percentage of rbc depleted=100% [(rbc count in sample tube)/(100% rbc count )].

EXAMPLE 3

Protocol for Magnetic Bead Depletion of Leukocytes 100 ml of $Na_4EDTA$-anticoagulated whole blood were collected, divided among 8 number of centrifuge tubes and centrifuged at 500 g for 10 minutes. The majority of plasma was removed and the buff colored layer of cells from each tube was removed, pooled together and centrifuged at 500 g for an additional 10 minutes. The buff colored cells and the plasma constitute the leuko-rich whole blood which should have an rbc count no greater than $8.0 \times 10_9$/ml and a white blood cell (wbc) of $2-4 \times 10_7$/ml.

100 μL of leuko-rich whole blood were pipetted into a number of reaction tubes. An amount of 10 to 160 μL of magnetic bead suspension (2.5% w/v) was then pipetted into each tube followed by the addition of 200 μL of 1X PBS. (N.B. Lower titer points with 10 to 40 μL of beads should be run first. Additional beads were added only if endpoint depletion was not obtained at 40 μL). Each tube was nutated for 3–5 minutes at low speed. 2 ml of 1X PBS were then added, the contents of a tube mixed and the beads then magnetically separated for 2 minutes. All supernatant liquid was removed and placed in a duplicate tube which was then centrifuged at 400 g for 5 minutes. The resulting supernatant was then carefully removed by pipette and analyzed.

The leuko-rich or the leuko-depleted whole blood samples were analyzed by the addition of 10 μL of single or dual color antibody preparation designed to discriminate for the depletion of specific cells from a mixture of cells. For example, when T11-conjugated magnetic beads were used in depletion, T11-B4 dual color was used to discriminate between actual T11 cell depletion and the non-specific depletion of T11 cells (i.e. B cells). The mixture was vortexed and incubated for 10 minutes at room temperature in the dark. Controls were isotype control and antibody control with undepleted cells. The tubes were then placed on a Coulter EPICS® Q-prep, or similar instrument, and run on the 35 seconds lyse mode. After the rbcs were lysed and the samples fixed (Q-prep), all samples were analysed on a Coulter EPICS® Profile flow cytometer or similar instrument. This procedure is required to obtain data as actual number of cells per volume of sample. Programs available on Profile were used to analyze lymphocyte and monocyte-myeloid populations.

Summary of Test Results using the Protocols of Examples 1–3.

1. In a T11/B4 lymphoid cell assay, the undepleted control gave 97,209 T11+, 18,240 B4+, 19,717 monocyte and 25,381 granulocyte counts. After depletion with 10 μL of 2.5% w/v solids magnetic beads conjugated with T11 antibody, the counts were 15,826, 20,181, 19,954 and 30,972 respectively. Depletion with 20 μL T11 antibody conjugated beads gave 2,256, 20,989, 20,874 and 31,965 counts; 30 μL gave 1,150, 21,428, 20,697 and 35,362 counts; and 40 μL gave 644, 21,232, 19,817, and 33,935 counts, all respectively.

2. In a T4/T8 lymphoid cell assay, the undepleted control, which contained $4.1 \times 10^5$ T8 and $7.9 \times 10^5$ T4 cells, gave 54,415 T4 and 27,906 T8 counts. After depletion with 10, 20 and 30 μL of 2.5% w/v/solids magnetic beads conjugated with T8 antibody the counts were 57,030 and 12, 59,538 and 6, and 60,905 and 5, respectively.

3. In an erythrocyte/thrombocyte assay, the undepleted control contained $4.5 \times 10^6$ wbc, $4.4 \times 10^8$ rbc and $4.7 \times 10^7$ platelets. Depletion experiments were conducted using 20, 40, 60 and 80 μL of 2.5% w/v solids magnetic beads conjugated with KC-16 antibody. The wbc, rbc and platelets remaining after depletion were 20 μL: $4.4 \times 10^6$ wbc, $1.6 \times 10^8$ rbc and $4.3 \times 10^7$ platelets; 40 μL: $4.6 \times 10^6$ wbc, $1 \times 10^7$ rbc and $4.5 \times 10^7$ platelets; 60 μL: $4.5 \times 10^6$ wbc, $1 \times 10^7$ rbc and $4.3 \times 10^7$ platelets; and 80 μL: $4.5 \times 10^6$ wbc, $1 \times 10^7$ rbc end $4.3 \times 10^7$ platelets. The results indicate that 40 μL of 2.5% solids beads which contained $1.85 \times 10^{10}$ particles removed $4.3 \times 10^8$ rbc, thus giving a particle-to-rbc ratio of 43.

4. In a myeloid cell assay, the undepleted control gave 73,821 lymphocyte, 13,426 monocyte and 55,661 granulocyte counts. Depletion studies were conducted using 10, 20, 30 and 40 μL of 2.5% w/v solids magnetic beads conjugated with KC-48 antibody. The results were 10 μL: 70,330, 9,309 and 340 counts; 20 μL: 68,414, 2,006 and 1,332 counts 30 μL: 62,966, 1,597, and 922 counts; and 40 μL: 59,340, 1,546 and 899 counts, all respectively.

A similar depletion study was conducted using 10, 20, 30 and 40 μl of of 2.5% w/v solids magnetic beads conjugated with 1D3 antibody. The results were 10 μL: 76,405, 13,839 and 1,597 counts; 20 μL: 73,198, 8,653 and 1,216 counts; 30 μL: 65,667, 2,590 and 2,130; and 40 μL: 66,276, 1,906 and 1,686 counts, all respectively.

A further depletion study was conducted using 10, 20, 30 and 40 μL of 2.5% w/v solids magnetic beads conjugated with MO2 antibody. The results were 10 μL: 72,563, 3,107 end 56,520 counts; 20 μL: 72,905, 3,616 and 34,533 counts; 30 μL: 69,644 1,618 and 32,313 counts; and 40 μL: 69,477, 1,210 end 30,899 counts, all respectively.

5. In an erythrocyte/thrombocyte assay, the undepleted control contained $7 \times 10^6$ wbc, $4.9 \times 10^{10}$ rbc and $3.0 \times 10^7$ platelets. Depletion studies were conducted using 20, 40, 60 and 80 μL of 2.5% w/v solids magnetic beads conjugated with PLT-1 antibody. The results, after depletion, were 20 μL: $10 \times 10^6$ wbc, $5.4 \times 10^{10}$ rbc and $1 \times 10^6$ platelets; 40 μL: $10 \times 10^6$ wbc, $5.8 \times 10^{10}$ rbc and $1 \times 10^6$ platelets; 60 μL: $7 \times 10^6$ wbc, $5.1 \times 10^{10}$ rbc and $1 \times 10^6$ platelets; end 80 μL: $10 \times 10^6$ wbc, $5.6 \times 10^{10}$ rbc and 0 platelets.

II. Preparation of Magnetic Particles Having A First Gelatin Layer and a Second Aminodextran Layer Preparation of Aminodextrans.

Method A. Small scale preparation of aminodextran.

Aminodextran was prepared by partial cleavage and oxidation of the glycopyranose rings in dextran to aldehyde functional group, coupling of the aldehyde groups with 1, 3-diaminopropane to form Schiff base linkages and reduction of the Schiff's base linkages to form stable carbon-nitrogen bonds. In a typical procedure, 20 g of dextran were dissolved in 150 ml of 50 mM potassium acetate buffer, pH 6.5. A solution of 2.14 g of sodium perioidate in 25 ml of distilled water was added dropwise to the dextran over about 10 minutes with vigorous magnetic mixing. The resulting solution was stirred at room temperature, 15–27° C., for about 1.5 hours and then dialyzed against distilled water. 20 ml of 1,3-diaminopropane were mixed with 20 ml of distilled water, cooled in an ice bath, vigorously stirred and pH adjusted from about 11.5 to about 8.7 over about 15 minutes by the addition of glacial acetic acid. Typically, 15–20 ml of glacial acetic acid was used. The dialyzed dextran solution was added dropwise over about 15–20 minutes to the chilled diamine solution. After the addition was completed, the resulting solution was stirred at room temperature for about 2.25 hours. A reducing solution of 0.8 g sodium borohydride in 10 ml of 0.1 mM sodium hydroxide was added to the dextran reaction mixture at room temperature over about 15 minutes. The reaction mixture was stirred during the borohydride addition to expel most of the effervescence. The crude aminodextran solution was exhaustively dialyzed against distilled water until the conductivity of the effluent was 3–4 μmho/cm. The dialyzed solution was then filtered through an 0.2 μm filter and freeze-dried over 24 hours in a model TDS-00030-A, Dura-Dry microprocessor controlled freeze-dryer (FTS Systems, Inc.) to produce 4.25 of flaky, pale yellow crystals in 21% yield.

Method B. Large scale preparation of aminodextran.

The procedure of Method A was modified for the large scale prepartion of aminodextran and for increasing the number of amino groups introduced into dextran. Hollow fiber membrane filtration replaces dialysis and a smaller diamine-periodate molar ratio was used to avoid further cleavage of the sugar polymer into lower molecular weight fragments. A hollow fiber cartridge (polysulfone, 3 ft$^3$ membrane surface area, 1 mm diameter fibers and 5,000 MW cut-off) was mounted vertically with an input power pump (two pump heads, maximum flow rate of about 4.56 liters/minute with No. 18 Norprene® food grade tubing) delivering 15–20 psi which corresponds to 5–10 psi in the retentate line. The filtrate was collected at 50–100 ml/min. Washing was done using 20–30 liters of distilled water over about 6–8 hours. The specific conductance was reduced to about 3–4 μmho-cm and the pH was 6.0–6.5. The feed volume was maintained at 2 liters during desalting and then concentrated to 800 ml in the first washing of oxidized dextran and to 400 ml in the second washing of aminodextran.

In a standard scaled-up preparation, 80 g of dextran were transferred to 1 quart [liter] glass blender bowl containing 600 ml distilled water. The solid was blended for about 2–5 minutes at medium speed to dissolve all the dextran. 8.56 g of sodium periodate were dissolved in 100 ml of distilled water and the resulting solution was added dropwise to the dextran solution over about 10 minutes using vigorous magnetic stirring. After the addition was completed, the resulting mixture was stirred at room temperature for an additional 3 hours. The resulting viscous reaction mixture was then diluted to 2 liters with distilled water and desalted using a hollow fiber cartridge. The initial specific conductance was 1.5 mmho-cm$^{-1}$ or higher and the initial pH was 4.0. About 18–22 liters of distilled water were used to obtain solution having a final pH of 6.0–6.5. The final volume of washed, oxidized dextran solution was 800 ml.

To the washed, oxidized dextran solution, 80 ml of colorless, liquid 1,3-diaminopropane were slowly added over about 10 minutes at room temperature. The resulting mixture was then stirred at room temperature for an additional 3 hours. After the stirring was finished, 3.2 g of sodium borohydride dissolved In 40 ml of 1 mM aqueous sodium hydroxide were added to the room temperature aminodextran reaction mixture over about 5 minutes with magnetic stirring. After the completion of the sodium borohydride addition, the resulting mixture was stirred for an additional 1 hour end then desalted using a hollow fiber cartridge. The Initial specific conductance was 5.0 mmhocm$^{-1}$ or higher and the initial pH was about 12.0. About 20–25 liters of distilled water were needed to reduce the specific conductance to about 3–4 μmho-cm$^{-1}$ and the pH to 6.0–6.5. The final volume of aminodextran solution was 400 ml. This solution was passed through a 0.2 μm sterile cellulose acetate filter unit and then freeze-dried over 48 hours to obtain 48 grams of flaky, pale yellow crystals, a 52% yield.

Elemental analysis (C,H,N) were obtained for two samples of aminodextran prepared from dextran T-2M by the methods described above. The analyses are:

Sample 1.20 g dextran scale, desalting by dialysis. Obsd.: C, 43.04; H, 6.60, N, 1.09; 0 (by difference), 49.27.

Sample 2.80 g dextran scale, desalting by membrane filtration. Obsd.: C, 42.53; H, 6.52 N,1.01; 0 (by difference), 49.94 Calculated for $C_{46}H_{79}NO_{37}.3H_2O$: C, 42.76; H, 6.63; N, 1.08; O, 49.53

The analyses for aminodextran in the two preparations were very similar, thus indicating that the same product was obtained whether desalting was done by dialysis or by membrane filtration. The empirical formula obtained for Sample 1, $C_{46}H_{84}NO_{40}$, is very similar to the formula $C_{46}H_{79}NO_{37}.3H_2O$ based on 29 units of glucose ($C_6H_{10}O_5$), 1 unit of fully diamine-substituted sugar ring ($C_{12}H_{28}N_4O_3$) and twelve units of water. Therefore, the degree of diamine substitution in dextran was 1/30 in Sample 1 in contrast to a theoretical value of 1/12 based on 100% periodate cleavage and diamine substitution. The empirical formula obtained for Sample 2, $C_{49}H_{90}NO_{43}$, is very similar to the formula $C_{49}H_{84}NO_{40}.3H_2O$ based on 31 units of glucose, 1 unit of fully diamine substituted sugar ring and twelve units of water. The degree of substitution in dextran by diamine was 1/32 for Sample 2.

In the preparation of aminodextran coated particles, similar results were obtained using aminodextrans having average molecular weights of 10,000, 40,000 and 2,000,000 (T-10, T-40 and T-2M) with 1X (1X=3.3% substitution of sugar residues), 2X (6.6%) 3X (9.9%) and 5X (16.5%) molar amounts of amino groups. All the aminodextrans were initially prepared according to methods A and B using 2 and 3 times the amount of sodium periodate used in the 1X oxidation of dextran. The amount of 1,3-diaminopropane used for Schiff base formation was kept constant.

Modifications have been made to the Methods A and B of preparing aminodextrans which were originally disclosed in Ser. NO. 07/827,347. These modifications involve the oxidation and cleavage of the dextran glucose rings with periodate anion, diamine addition and sodium borohydride reduction of the Schiff's base. The modifications have led to increased yield on the aminodextrans, particularly the 5X -aminodextran. Generally, the first modification was to use only a ten percent (10%) excess of diamine over the stoichiometric 2:1 diamine:periodate molar ratio previously disclosed. Second, the diamine addition reaction was conducted at a temperature in the range of about 5–10° C. Third, the diamine addition reaction was spectroscopically monitored in the near ultraviolet (UV) region for Schiff base formation. Schiff's base formation was deemed completed when successive spectral analyses indicated e plateau was reached. The reaction was then stopped. These modifications reduced aminolysis of the polymeric sugar groups into lower weight fragments and thus gave higher yield of product after purification and concentration by hollow fiber membrane filtration. The hollow fiber filtration was done using polysulfone cartridge of 3 ft$^2$ membrane surface area, 1 mm diameter fiber having a 5,000 molecular weight cut off. The cartridge was mounted vertically in an input power pump having two pump heads delivering 15–20 psi with s maximum flow rate of 4.56 liter/minute when using No. 18 Norprene® food grade tubing. With this configuration, the pressure in the retenate line was about 5–10 psi. The filtrate was collected at 50–100 ml/min. Washing was done using 20–30 liters of distilled water over about 6–8 hours. The following method for preparing 5X-aminodextran is given to illustrate the modified procedure which is applicable to the preparation of all aminodextrans.

Method C. Preparation of 5X-Aminodextran.

T-2M dextran (50 g, 0.308 mol, obtained from Sigma or Pharmacia) was added to a 1-quart or 1-liter glass blender bowl containing 300 ml of distilled water. The mixture was blended at maximum speed until all the dextran dissolved, typically about 3–5 minutes. A solution of 26.75 g (0.125 mol) of $NaIO_4$ in 300 ml distilled water was added to dextran solution over about a 10 minute period using vigorous magnetic stirring. After the periodate addition was completed, the reaction mixture was stirred at room temperature for about an additional three hours. After the three hours, the 600 ml reaction volume had an specific conductivity of 9.7 mmho-cm$^{-1}$ and an initial pH of 2.5. The reaction mixture was diluted to two liters distilled water and desalted using the hollow fiber cartridge. Washing was done using 15–18 liter of water to obtain 600 ml of washed, oxidized dextran solution having a specific conductance of 10 mmho-cm$^{-1}$ end pH of 6.7.

The solution of oxidized dextran was cooled to about 8° C. using an ice bath and 23.2 ml (0.275 mol) of diaminopropane was added over about 10 minutes to the oxidized dextran solution. The resulting reaction mixture was stirred and maintained at the ice bath temperature. The formation of the yellow Schiff's base was monitored ever 10–15 minutes by measuring the 335 mm near UV absorbance of an extracted smaple. In a typical experiment, the measurements at 335 nm using a 1mm path length cell were:

TABLE 1

| minutes | absorbance values |
|---|---|
| 0 | 0.100 |
| 5 | 2.063 |
| 15 | 2.975 |
| 30 | 3.692 |
| 45 | 3.901 |
| 60 | 4.103 |
| 75 | 3.784 |

After the absorbance had reached a plateau, 19.3 g (0.500 mol) of sodium borohydride in 19.3 ml of 1 mM aqueous potassium hydroxide were added to the reaction mixture over about 10 minutes at ambient temperature with magnetic stirring. After the sodium borohydride addition was completed, the reaction mixture was stirred at ambient temperature for about an additional two hours. After the stirring was completed, spectroscopic measurement at 335 nm using a 1 cm path length cell gave an absorbance value of 0.067 units which indicates that the Schiffis base compound had essentially disappeared. The reaction mixture, about 1000 ml volume, was then desalted using the hollow fiber cartridge. The initial specific conductance was 43 mmho-cm$^{-1}$ and the initial pH was 11.0. About 18–20 liters of distilled water were used as wash liquid to produce about 300 ml of 5X-aminodextran solution having a specific conductance of about 4–6 μmho-cm$^{-1}$ and a pH of 6.5–7.0. The 5X-aminodextran solution was filtered through a 0.2 μm cellulose nitrate filter and freeze-dried over 48 hours in a model TDS-00030-A, Dura-Dry® microprocessor-controlled freeze-dryer (FTS Systems, Inc.) to produce 24 g (48% yield) of flaky, pale yellow crystals. Elemental analysis: C=45.83%, H=7.00%, N=4.49%, O (by difference)= 42.68%. Calculated analysis for $C_{12}H_{22}O_{8.25}N$: C=46.15%, H=7.10%, N=4.48%, 0=42.26%.

The empirical formula based on actual analysis is $C_{12}H_{22}O_{8.3}N$, which is very similar to the formula $C_{12}H_{22}O_{8.25}N$ based on 6 units of glucose per one unit of fully dismine-substituted sugar ring ($C_{12}H_{28}N_4O_3$). Therefore, the degree of diamine substitution in dextran was 1/7 in contrast to a theoretical value of 1/2.5 based on 100% periodate cleavage and diamine substitution. Repeat experiments at 200 g and 300 g dextran scales produced a product having the same degree of substitution.

Preparation of Magnetite and Other Magnetic Particles An Gelatin Solution.

Metal ferrites ($MFe_2O_4$ where M=$Fe^{2+}$, $Mm^{2+}$, $Zn^{2+}$, $Co^{2+}$, $Ni^{2+}$and $Ba^{2+}$) including magnetite can be prepared in situ in type B gelatin as described in I above. To further illustrate the invention, manganese ferrite was prepared as follows.

62.5 mmol (62.5 ml) of 1M $Fe_2SO_4$ solution, 100 mmol (50 ml) of 2M $KNO_3$ solution, 31.25 mmol (31.25 ml) of 1M $MnSO_4$ solution and 72.92 ml of distilled water were mixed together in a one liter Pyrex® bottle and purged with $N_2$ gas for 10 minutes (Solution A). Then, 166.6 mmol (33.33 ml) of 5M KOH was added to Solution A, swept with $N_2$ gas and sonicated at room temperature (18–27° C.) for a time in the range of about 5–10 minutes to yield a smooth, dark green slurry of $Fe(OH)_2$ gel. After sonication, 250 ml of 2% type B, alkali cured, 225 Bloom bovine skin gelatin solution were added to the $Fe(OH)_2$ gel, mixed, swept with $N_2$ gas, capped tightly, sonicated for about 5–10 minutes and placed undisturbed in a 90° C. oven for about 24 hours. After oven heating, the Pyrex® bottle and contents were removed from the oven and allowed to cool to room temperature. After cooling was completed, the suspension of brown particles in the bottle was mixed and decanted into two 250 ml tissue culture flasks. The fraction in each flask was washed about five times with 1% w/v type B gelatin or with 1% 1X aminodextran solution using magnetic separation between washings. After washing, the magnetic particles were recombined, suspended in sufficient 1% 1X-aminodextran solution to make 500 ml total volume and sonicated for about 0.5 hour. The particles were stored at refrigeration temperatures of about 5–100 C. for 8 time of 8 hours to at least six months. Storage was done as a 2.5% w/v solids suspension in 1X-aminodextran solution containing 0.1% w/v sodium azide. Alternatively, the particles may be used immediately after preparation in type B gelatin and washing with 1X-aminodextran.

Preparation of 5X-Aminodextran Coated Magnetic Particles.

Method 1. A quantity of stored manganese ferrite particles prepared according to the procedure described above and of uniform 0.3 μm size and spherical shape were washed a plurality of times with distilled water, dried at 105° C. and the w/v solids in suspension was determined. A sample which analyzed as having 0.56% w/v solids was used herein.

100 ml of 0.56% w/v solids, gelatin prepared, aminodextran-stored manganese ferrite particles were magnetically separated and resuspended in an equal volume of 2% w/v 5X-aminodextran solution. The 100 ml suspension of brown particles was sonicated for about 10 minutes and then mixed overnight (about 8–16 hours) in a 250 ml tissue culture flask on an orbital shaker. After the mixing was completed, the pH was adjusted to 10.0 with about 20 µL of 5M aqueous potassium hydroxide. The adsorbed 5X-aminodextran was crosslinked by the addition of 1.173 ml of 25% aqueous glutaraldehyde (3.11 mmol) to the pH adjusted particle suspension and mixing the resulting suspension for a time in the range of 1–4 hours, preferably one hour, using an orbital shaker. The crosslinked particles were magnetically separated, the supernatant measured and discarded, and, to block and stabilize unreacted aldehyde groups, the particles resuspended in a volume of 1% 5X-aminodextran solution equal to that of the discarded supernatant. Alternatively, a polyamine solution such as ethylenediamine or 1,3-diaminopropane solution may be used to block the unreacted aldehyde groups. The molar amount of polyamine is about ten times the amount of glutaraldehyde used. The resuspended particles were shaken and sonicated to disperse them, and the resulting suspension was mixed overnight using an orbital shaker. A 23.5 ml sample of 10 mg/ml sodium borohydride (6.22 mmol $NaBH_4$) in 1 mM aqueous potassium hydroxide was then added to the suspension and the resulting mixture orbitally mixed for an additional 0.5 hour. The particles were then magnetically separated and washed a plurality of times (minimum three) with 1X PBS and concentrated to 22.4 ml volume to yield a 2.5% w/v solids suspension.

Method 2. A 60.2 ml sample of 0.83% w/v solids manganese ferrite particles suspended in 1% w/v 1X-aminodextran solution containing 0.1% sodium azide was magnetically separated and washed a plurality of times with 20 ml portions of 0.2M aqueous sodium chloride. After washing, the particles were resuspended in sufficient 3.75 mg/ml 5X-aminodextran in 0.2M sodium chloride solution (about 20 ml) to give a 2.5% w/v solids suspension. Next, for each milliliter of the 2.5% w/v solids suspension, 9 µL of 10 mg/ml EDAC.HCl in 0.2M sodium chloride solution was added to the suspension (180 µL total). The resulting mixture was orbitally shaken in a 50 ml tissue culture flask for a time in the range of about 12–16 hours. The particles were magnetically separated, washed a plurality of times with distilled water and resuspended in 1X PBS to yield 20 ml of 2.5% w/v solids suspension of magnetic particle having a coating formed by a condensation reaction between gelatin and the aminodextran. This condensation reaction occurs between aminodextran amine groups and carboxylate groups present on the gelatin. EDAC removes the water which is formed during the condensation reactions as a urea. The use of a crosslinking agent such as glutaraldehyde is not necessary. The resulting particles are defined as being equivalent to particles having a first gelatin layer, a second aminodextran layer and crosslinked by a chemical crosslinking agent.

Determination of Crosslinked Gelatin and 5X-Aminodextran Layer Thickness.

A. Gelatin Thickness.

A glutaraldehyde crosslinking solution was prepared by mixing 56 µL of 25% aqueous glutaraldehyde with 5 ml of 1 mM aqueous potassium hydroxide. The particles from 5 ml of a 2.5% w/v solids suspension of manganese ferrite particles prepared in type B gelatin as described and suspended in 2% w/v, type A, 175 Bloom gelatin in 0.1M phosphate buffer solution, pH 8.4, were magnetically separated and the supernatant liquid discarded. The separated particles were resuspended in 5 ml of the glutaraldehyde solution and mixed, preferably using a roller mixer, for about 30 minutes. The particles were again magnetically separated and washed three times with 5 ml of 1 mM aqueous potassium hydroxide before resuspension in 5 ml of 1 mM aqueous potassium hydroxide.

Elemental analysis was performed using 5 ml of crosslinked, gelatin coated manganese ferrite particles that were washed fifteen times with distilled water and dried to constant weight at 1100° C. Analytical results were: Mn=19.05%, Fe=49.49%, C=0.54%, H<0.5%, N<0.5% and O (by difference)=30.92%. The percentage of carbon weight in gelatin can be obtained from its amino acid content (The Theory of the Photographic Process, 4th T. H. James, ed (Macmillan, New York 19767), Chapter 2, page 52. The type A gelatin used herein gives C=50.46%, H=6.765%, N=18.27%, O=24.29% and S=0.21%. Using this information, the gelatin layer thickness can be calculated.

Using 1 g of gelatin coated ferrite particles, there will be 1 g×0.0054/0.5406=0.01070 g gelatin and 0.9893 g ferrite. The particle volume of a 0.29 µm diameter manganese ferrite sphere is $1.277 \times 10^{-14}$ cm$^3$ and the number of particles in 0.9893 g manganese ferrite is $1.827 \times 10^{13}$. Consequently, the mass of gelatin per ferrite particle is $5.856 \times 10^{-16}$ g.

Assuming a density of gelatin coating of 0.02 g/cm from the 2% w/v gelatin before crosslinking with glutaraldehyde, the volume of gelatin per particle is $2.92 \times 10^{-14}$ cm$^3$. As a result, the total volume, gelatin plus ferrite, per particle is $4,205 \times 10^{-14}$ cm$^3$ and the radius of a gelatin-ferrite sphere As $2,157 \times 10^{-5}$ cm (0.2157 µm). The thickness of the gelatin coating on the manganese ferrite sphere is thus 0.2157 µm–0.145 µm (the mean radius of the ferrite sphere)=0.0707 µm (71 mm). This is in good agreement with the values of 750 Angstroms on glass given A. T. Kudish et al., Proteins at Interfaces, ACS Symposium Series 343, J. L. Brash et al., eds. (American Chem. Soc., Washington, D.C. 1987), pages 261–277; 75 nm on mica given by N. Kawanishi, et al., J. Phys. Chem. 94:4611–4617 (1990); and 600–700 Angstroms on glass given by H. Metzer et al., J. Colloid Interface Sci. 126:292–303 (1988).

The gelatin layer thickness was similarly calculated for manganese ferrite particles where the gelatin layer was crosslinked using polyvinylpyrrolidone (PVP) stabilizer. Elemental analysis gave: Mn=18.84%, Fe=47.82%, C=1.67%, H<0.5, N<0.5 and O (by difference)=31.67. The calculated thickness of the gelatin coating was calculated as 148 mm. The thicker coating using PVP is believed to result from procedural differences. The thicker coating was obtained when the ferrite-gelatin solution is diluted, in the original procedure, from 2% to 0.08% and 1% PVP is added. The thinner coating was obtained when the gelatin-ferrite particles were separated from the 2% gelatin solution and resuspended in the crosslinking medium. As a result, there was no excess polymer, either gelatin or PVP, present.

B. Aminodextran Thickness.

Manganese ferrite particles were coated with 5X-aminodextran (Method 1) which was subsequently crosslinked, blocked end stabilized. The resulting particles were washed a plurality of times with distilled water, magnetically separated and dried at 110° C. Elemental analysis results were: Mn=14.04%, Fe=44.36%, C=2.97% and O (by difference)=38.63%. For 5X-aminodextran analyzed as containing 45.83% C and a 2% w/v 5X-aminodextran coating, the estimated aminodextran layer has a thickness of 218 mm.

Activation of Diamine Treated Particles with Sulfo-SMCC.

The same procedures described for activating gelatin coated particles with sulfo-SMCC are used to activate the 5X-aminodextran coated particles except that five times the activating amount of sulfo-SMCC were used. When the magnetic particles are coated with 1X -, 2X- or 3X-aminodextran, one, two or three times the amount of sulfo-SMCC is used, respectively.

Antibody Activation with 2-Iminothiolane Hydrochloride.

Antibodies were activated with 2-iminothiolane hydrochloride according to the procedures previously described herein. If the antibody or other substance which is to be conjugated to the activated particles has a sufficiency of reactive sulfhydryl group, activation by 2-iminothiolane hydrochloride may not be necessary. Those skilled in the art will also recognize that the activation of particles to contain maleimidyl groups and the activation of antibodies or other substances can be switched. That is, the particles can be activated by the introduction of reactive sulfhydryl groups and the antibody or other substance can be activated to contain reactive maleimidyl groups.

The following example is given to illustrate the utility of the invention and are not to be taken as limiting the invention. Unless otherwise indicated, Method 1 was used to coat particles with 5X-aminodextran in this example, two methods for enumerating neutrophils in a leukocyte-rich (leuko-rich) whole blood sample are described. The monoclonal antibody 1D3 conjugated to 5X-aminodextran coated beads and flow cytometry is used in both methods.

In the first method, a series of 1D3 containing magnetic bead titers were prepared, mixed with the leuko-rich blood sample and then magnetically separated from the sample. The neutrophil-depleted supernatants were then analyzed by flow cytometry to determine the point at which neutrophil depletion was complete. Samples were analyzed in the order of lowest titer to highest titer and depletion was recognized by a constant cytometer count.

In the second method, whole blood samples were mixed with the same titers of 1D3-conjugated magnetic beads, but no magnetic separation was performed. The mixtures were analyzed by flow cytometry for neutrophils shifted out of the normal granulocyte region in the forward versus side (orthogonal) scatter histogram because of s change in cell size, shape or refractive index due to attachment of magnetic beads to the neutrophil cell surfaces. When the shifted neutrophil population or count reached a plateau value, its count in the light scatter histogram or its fluorescent event count in the bitmapped region was compared to the respective counts for all white blood cells (lymphocytes, monocytes and granulocytes) to obtain the relative number of neutrophils.

The use of well-defined ferrite particles of uniform size, uniform spherical shape and uniform refractive index properties is essential in obtaining a recognizable, definitive shift in light scatter from biological cells conjugated to the surface of particles such as the particles described herein. In addition to electric dipole scattering arising from chemical substances, magnetic dipole scattering from the ferrite particles can make a substantial contribution to the intensity of the light scattering arising from the cell-particle conjugates [J. A. Stratton, Electromagnetic Theory (McGraw Hill, New York 1941), page 437, and C. F. Bohren and D. R. Huffman, Adsorption and Scattering of Light by Small Particles (Wiley, New York 1983), page 141]. J. J. Murry, Optics 4:1011 (1965), has measured low angle light scattering by magnetic particles such as magnetite.

The diameter of the manganese ferrite particles which are used herein was $0.29 \pm 0.08$ μm. This diameter lies outside the mean diameter range of 0.65–3.0 μm for the polystyrene latex and magnetic latex particles which were used in International Patent Application Publication WO 90/13013 entitled METHOD AND APPARATUS FOR SCREENING CELLS OR FORMED BODIES WITH POPULATIONS EXPRESSING SELECTED CHARACTERISTICS UTILIZING AT LEAST ONE SENSING PARAMETER and PCT Application No. PCT/US/08590 (to Coulter Corporation, the assignee herein) entitled METHOD AND APPARATUS FOR SCREENING NICROSCOPIC CELLS UTILIZING LIGHT SCATTER TECHNIQUES. The polystyrene latex particles used in these studies were of uniform size and shape. However, while the magnetic latex particles, which were formed by embedding ferrofluid particles of varying size and shape inside the latex during emulsion polymerization (U.S. Pat. No. 4,358,388 to Daniel et al.), were spherical in shape, they varied widely in size. For example, while the mean particle diameter was 0.7 μm, individual particles varied from 0.2 μm to 1.0 μm. (An additional problem arises from the fact that the structure of the ferrofluid particles embedded in polystyrene latex is not definable.) The small diameter particles, though low when measured by weight percent, were very numerous. Consequently, due to the higher mobility of the smaller particles relative to the mobility of the larger particles, the smaller particle-antibody conjugates will preferentially occupy antigenic sites on cell surfaces. However, the contribution of these small particles toward shifting the light scatter of cells is minimal and the use of these magnetic particles to obtain a true enumeration or count of targeted shifted cell populations is unreliable. This may, in part, be due to a resultant low net magnetic dipole when a summation is carried over many magnetic particles of different spacial orientation within the latex particles.

In addition to their uniform size and uniform spherical shape, the index of refraction of dense, microcrystalline ferrite particles that are formed and coated as described here is sufficiently different from the index of refraction of polystyrene latex and biological cells. When selected cell sets or subsets are coupled to these magnetic particles, large shifts occur in the forward versus side scatter histograms of the conjugated cells relative to the histogram of unconjugated cells. Consequently, cells conjugated to the particles can be distinguished from those not conjugated to particles.

EXAMPLE 4.

Enumeration of Neutrophils

Preparation of Samples.

A 50 ml sample of $Na_4EDTA$-anticoagulated whole blood was divided among a plurality of centrifuge tubes and centrifuged at 500g for about 10 minutes. The majority of the plasma was removed and the buff colored layer of cells in each tube was removed, pooled and centrifuged again at 500 g for about 10 minutes. Collectively, the buff colored cells and the plasma constitute the leuko-rich whole blood which should have a red blood cell (rbc) count no greater than $8.0 \times 10_8$/ml and a white blood cell (wbc) count between $2–4 \times 10_7$/ml.

100 μL of the leuko-rich buff colored cells were pipetted into a plurality of reaction tubes. A quantity of 5 to 250 μL of 2.5% w/v suspended solids, 1D3-conjugated, 5X-aminodextran coated manganese ferrite particles prepared as described herein was pipetted into separate tubes. Typically the titers of ferrite particle suspension were 0, 5, 10, 20, 30, 40, 50, 75, 100, 150, 200 and 250 μL. The volume of each tube was then made up to 350 μL by the addition of 1X PBS. Each tube was nutated for 6 minutes at low speed and the contents of each tube were magnetically gathered and separated for 60 seconds. The supernatant liquid which constitutes a leukocyte-depleted (leuko-depleted) sample was carefully removed by pipette end placed in duplicate tube for analysis.

Leuko-rich (undepleted) and leuko-depleted buff colored cell samples were flow cytometrically analyzed to discriminate between actual neutrophil depeletion and non-specific neutrophil depletion; that is, depletion of lymphocytes, monocytes, eosinophils and basophils in addition to neutrophils. Each sample undergoing analysis was treated by the addition of 10 μl of the single color antibody reagent CYTO-STAT® KC56-FITC (Coulter Corporation, Hieleah, Fla.), vortexed and incubated for 10 minutes at room temperature. The control samples were isotype control and antibody control conjugated to undepleted buff colored cells. The tubes were then placed in a Counter EPICS® Q-prep or similar instrument and processed on the 35 second lyse mode. After the rbcs were lysed and the samples fixed (Q-prep), the total volume of each sample was 1,100 μL. All samples were then analyzed on a Coulter EPICS® Profile II flow cytometer or similar instrument. The programs available on the Profile II instrument were used to analyze lymphocyte and monocyte-myeloid populations as fluorescent events. To estimate the number of cells per volume of sample, the wbc count of the undepleted sample was determined on a Coulter S-Plus® counter ($4.19 \times 10^6$ wbc), 100 μL sample aspiration, and was compared with the total fluoresecent events measured ($1.81 \times 10^6$) for lymphocytes, monocytes end granulocytes in the undepleted sample and 100 μL sample aspiration. As s result of these measurements, the fluorescent events determined for the depleted samples were scaled by a factor of 2.31 [($4.19 \times 10^6$)÷($1.81 \times 10^6$)] and a dilution factor of 11 to obtain actual cell counts.

Procedure 1. Flow Cytometry Analysis for Neutrophils After Magnetic Bead Depletion of Samples.

A myeloid cell assay of an undepleted control sample resulted in 29,131 lymphocyte, 19,282 monocyte and 116,479 granulocyte counts as fluorescent events. The granulocytye percentage in the total wbc population is therefore 70.6%. Results obtained using the Coulter S-Plus® counter gave a granulocyte total of 71.7%. Depletion analysis was done using 5, 10, 20, 30, 40, 50, 75, 100, 150, 200 and 250 μL of 0.25% w/v solids magnetic beads conjugated with 1D3 monoclonal antibody. The results (Table 2) were:

TABLE 2

| | Counts | | |
|---|---|---|---|
| μL Beads | lymphocytes | monocytes | granulocytes |
| 5 | 32,428 | 11,638 | 106,421 |
| 10 | 32,243 | 9,971 | 86,017 |
| 20 | 32,200 | 5,477 | 42,296 |
| 30 | 33,884 | 4,178 | 31,505 |
| 40 | 30,788 | 2,166 | 23,008 |
| 50 | 30,707 | 1,597 | 16,117 |
| 75 | 29,914 | 1,373 | 13,471 |
| 100 | 28,327 | 961 | 10,645 |
| 150 | 24,427 | 701 | 8,127 |
| 200 | 21,127 | 512 | 7,147 |
| 250 | 16,933 | 470 | 6,397 |

Both neutrophils and monocytes were depleted throughout the titer with 1D3-conjugated magnetic beads. Monocyte removal can be avoided or substantially reduced by shortening the nutation time for the buff cell and magnetic bead mixture from 6 minutes to 30 seconds and reducing the magnetic separation time from 60 seconds to 15 seconds. Based on the difference between undepleted and depleted sample fluorescent events for granulocytes and the total wbc fluorescent events in the undepleted sample, the percentage of neutrophils in the total wbcs was 66.8%.

The neutrophil depletion data were converted to bead and cell values using a value of $4.18 \times 10^{10}$ manganese ferrite particles/ml of 0.25% w/v solids suspension and the factor 25.41 (the fluorescent event scale factor 2.31 times the dilution factor 11, both obtained above) to convert fluorescent events to granulocyte cell counts. These resulting values (Table 3) are:

TABLE 3

| μL Beads | No. Magnetic Beads × $10^8$ | No. Neutrophils Depleted × $10^6$ | Bead-to-Cell Ratio × $10^2$ |
|---|---|---|---|
| 5 | 2.1 | 0.26 | 8.1 |
| 10 | 4.2 | 0.77 | 5.5 |
| 20 | 8.4 | 1.9 | 4.4 |
| 30 | 12.6 | 2.2 | 5.7 |
| 40 | 16.8 | 2.4 | 7.0 |
| 50 | 21 | 2.6 | 8.1 |
| 75 | 31.5 | 2.6 | 12.1 |
| 100 | 42 | 2.7 | 15.6 |
| 150 | 63 | 2.8 | 22.5 |
| 200 | 84 | 2.8 | 30 |
| 250 | 105 | 2.8 | 37.5 |

FIG. 1, which graphically depicts the number of neutrophils depleted versus the magnetic bead-to-cell ratio, shows that a plateau in neutrophil depletion was reached between the 100 μL and 150 μL 0.25% w/v magnetic bead titers when $2.8 \times 10^6$ neutrophils were completely depleted using a bead-to-cell ratio of about 2000:1. This represents 66.8% of the total wbc count of $4.19 \times 10^6$ determined by the Coulter S-Plus® counter.

Procedure 2. Flow Cytometry Analysis for Neutrophils Shifted by Magnetic Beads.

Leuko-rich buff cell-magnetic bead mixtures were prepared as described in the Preparation of Samples for analysis using a Coulter Profile II cytometer, but no magnetic separation was done. Programs were introduced into the profile to analyze lymphocyte and monocyte-myeloid populations in the forward versus side scatter histogram; in particular, those neutrophils shifted out of the normal granulocyte region due to a change in size, granularity or refractive index brought about by binding the neutrophils to the magnetic ferrite particles. The series of histograms in FIG. 2 show a distinct and progressive shift toward less forward scatter (FS) or smaller size and more side scatter (LSS) or greater granularity in the normal granulocyte region as higher titera of magnetic beads were added to the cell samples.

The refractive index and magnetic properties of ferrite particles can, however, upset the usual trend to larger size (greater FS) and greater granularity (larger LSS) expected as particles are attached to targeted cells. Monocytes were shifted in the same direction as the granulocytes with the end result that at the highest magnetic bead titers they occupied the region normally occupied by granulocytes. Lymphocytes remained unshifted until titers greater than 100 μL of 0.25% solids magnetic beads were used. At these higher titers, lymphocytes were apparently removed because there is a shift out of the lymphocyte boxed region of the forward versus side scatter histogram. This apparent shift occurs when there is present an excess of magnetic beads not bound to either monocytes or neutrophils. The excess beads appear to disturb the granularity of lymphocytes not by binding them, but by back-scatter from the excess magnetic ferrite particles. The following Table 4 gives the original granulocyte count, the shifted granulocyte count and the percent of granulocytes shifted using different titer of 0.25% w/v solids, 1D3 conjugated, 5X -aminodextran coated manganese ferrite particles.

TABLE 4

| μL Beads | Granulocyte | | |
|---|---|---|---|
| | Original Count | Shifted Count | % Shifted |
| 0 | 120,977 | 10,413 | 0 |
| 5 | 121,892 | 16,537 | 11.9 |
| 10 | 115,195 | 31,918 | 21.7 |
| 20 | 87,148 | 55,773 | 39.0 |
| 30 | 84,669 | 60,156 | 41.6 |
| 40 | 73,559 | 74,978 | 50.5 |
| 50 | 54,482 | 72,032 | 56.9 |
| 75 | 16,987 | 80,129 | 82.5 |
| 100 | 17,449 | 88,145 | 83.5 |
| 150 | 14,766 | 87,669 | 85.6 |
| 200 | 9,720 | 84,772 | 89.7 |
| 250 | 7,396 | 76,362 | 91.2 |

For the 100 μL titer, the total analysis results were 26,604 lymphocytes counts, 1,045 monocytes counts 17,449 unshafted granulocytes counts and 88,145 shafted granulocyte counts. As a result, the percent neutrophils in the total wbc count was calculated as 66.2%. The neutrophil percentage obtained by the population shaft method agrees well with the 66.8% calculated from the magnetic depletion data obtained using Procedure 1.

To further illustrate the utility of the invention, additional depletieon studies where performed on (a) red blood cells and platelets, and (b) white blood cells.

EXAMPLE 5

Magnetic Bead Depletion of Red Blood Cells and Platelets.

100 μL of Na$_4$EDTA-anticogulated whole blood were placed in a plurality of reaction tubes. Titers of 20–160 μL of 2.5% w/v solids, KC-16 conjugated, 5X -aminodextran coated manganese ferrite particles were added to the reaction tubes and the total volume in each tube was adjusted to 260 μL with 1X PBS. The resulting mixtures were nutated for 6 minutes in either a multi-tube vortexer or a single tube nutator at low mixing speed. When nutation was completed, the beads in each tube were magnetically separated for 60 seconds. The supernatant liquid was removed using a Pasteur pipette and was saved An iabelled tubes. The samples were analyzed using a Coulter S-Plus® or similar rbc counter as the total rbc count per 100 μL of sample (whole blood plus beads plus 1X PBS). The positive control was 100 μL whole blood plus 160 μL 1X PBS to gave 100% rbc count. The percentage rbcs depleted=100%−[rbc count in sample tube)÷(100% rbc count)].

The following Table 5 summarizes the results of an erythrocyte/thrombocyte assay. The 0 μL data is the undepleted control sample. The depletion was done using 1.25% w/v solids, KC-16 conjugated, 5X -aminodextran coated beads. KC-16 monoclonal antibody binds only to erythrocytes and does not bind leukocytes or platelets.

TABLE 5

| μL Beads | Counts | | |
|---|---|---|---|
| | wbc × 10$^5$ | rbc × 10$^8$ | platelets × 10$^6$ |
| 0 | 2.1 | 1.71 | 7.2 |
| 20 | 2.1 | 1.34 | 7.1 |
| 40 | 2.1 | 0.89 | 7.1 |
| 60 | 2.3 | 0.54 | 7.8 |
| 80 | 2.4 | 0.36 | 8.1 |
| 100 | 2.4 | 0.25 | 8.0 |
| 120 | 2.5 | 0.15 | 8.5 |
| 140 | 2.3 | 0.04 | 8.5 |
| 160 | 2.3 | 0.03 | 8.3 |

Figure 3:
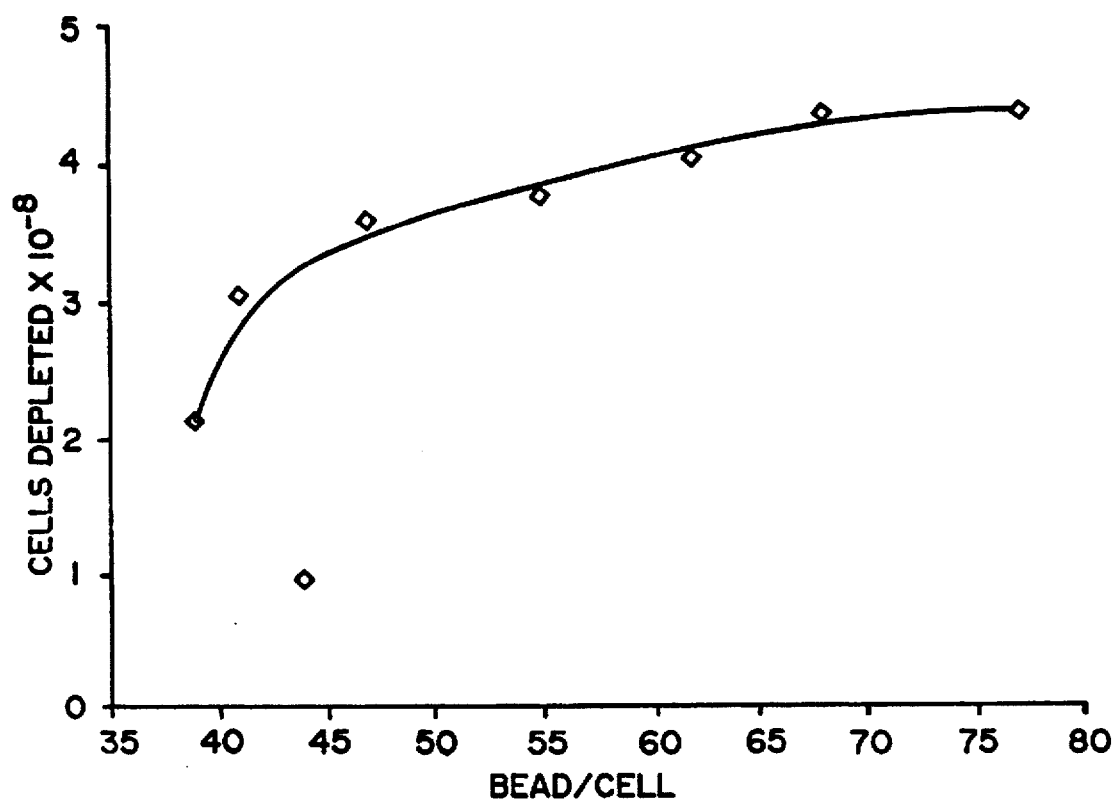
FIG. 3 is a plot of the number of red blood cells depleted versus the magnetic bead-to-cell ratio.

The number of magnetic beads/ml for a 2.5% w/v solids suspensions is $4.18 \times 10^{11}$. Using FIG. 3 a plot of the number of rbcs depleted versus bead-to-cell ratio, 160 μL of 1.25% w/v solid beads contained $3.36 \times 10^{10}$ magnetic particles and removed $4.37 \times 10^8$ rbcs, thus giving a particle-to-(bound rbc) ratio of 77.

The assay was repeated for magnetic beads coated with 5X-aminodextran by Method 2. The assay was performed using 5, 10, 20, 40, 60, 80, 100, 150, 200 and 250 μL titers of 2.5% w/v solid, KC-16 conjugated, 5X -aminodextran coated manganese ferrite particles. The positive control was 100 μL of whole blood in 250 μL 1X PBS which was subsequently diluted to 1.000 ml with 1X PBS. The wbc, rbc and platelet counts for the undepleted control are listed in the following depletion Table 6 as 0 μL beads.

TABLE 6

| μL Beads | Counts | | |
|---|---|---|---|
| | wbc × 10$^4$ | rbc × 10$^7$ | platelets × 10$^6$ |
| 0 | 8 | 4.7 | 1.8 |
| 5 | 8 | 4.5 | 1.9 |
| 10 | 8 | 4.4 | 1.8 |
| 20 | 8 | 37 | 1.8 |
| 40 | 8 | 2.3 | 1.7 |
| 60 | 7 | 1.5 | 1.8 |
| 80 | 7 | 0.9 | 2.1 |
| 100 | 6 | 0.6 | 1.8 |
| 150 | 6 | 0.4 | 1.8 |
| 200 | 6 | 0.2 | 1.7 |
| 250 | 6 | 0.1 | 1.8 |

A plot of number of rbcs depleted versus particle-to-cell ratio will have a plateau similar to that shown in FIG. 2. 150 μL of 2.5 w/v solids magnetic particles, at the plateau, contained $6.3 \times 10^{10}$ particles and removed $4.3 \times 10^8$ rbcs for a particle-to-rbc ratio of 147.

A depletion assay for platelets was performed and 10, 20, 30, 40, 50, 100, 150 and 200 μL of 0.83% w/v solids, PLT-1 monoclonal antibody (Coulter Corporation, Hialeah, Fla.) conjugated, 5X -aminodextran coated manganese ferrite particles. Total volume was adjusted to 350 μL by the addition of 1X PBS as needed. The positive control was 100 μL of whole blood diluted with 250 μL of 1X PBS. The wbc, rbc and platelets for the undepleted control are listed in the following depletion Table 7 as 0 μL beads.

TABLE 7

| µL Beads | Counts wbc × 10⁵ | rbc × 10⁸ | platelets × 10⁶ |
|---|---|---|---|
| 0 | 1.7 | 1.51 | 5.2 |
| 10 | 1.6 | 1.48 | 3.1 |
| 20 | 1.6 | 1.51 | 1.2 |
| 30 | 1.5 | 1.50 | 0.4 |
| 40 | 1.4 | 1.55 | 0.3 |
| 50 | 1.3 | 1.45 | 0.2 |
| 100 | 1.1 | 1.57 | 0.1 |
| 150 | 1.1 | 1.46 | 0.1 |
| 200 | 1.0 | 1.49 | 0.1 |

Figure 4:
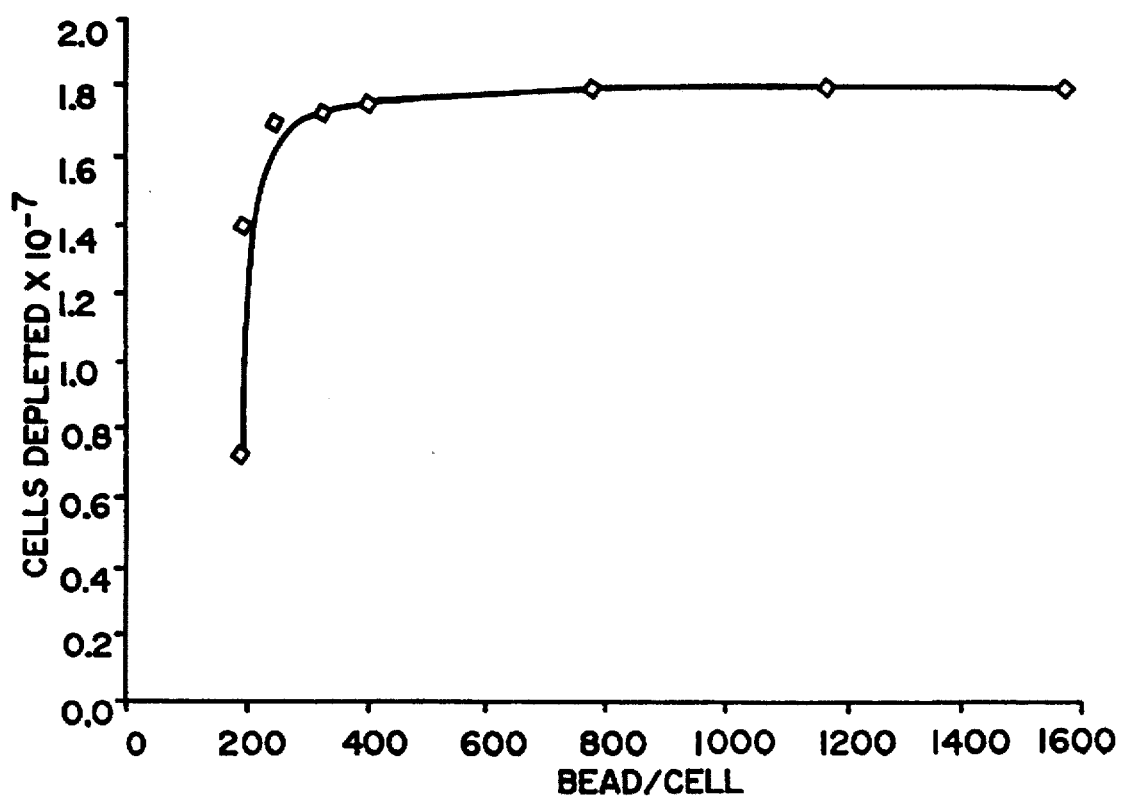
FIG. 4 is a plot of the number of depleted cells versus the magentic bead-to-cell ratio.

The results as plotted in FIG. 4 indicate that 100 µL of 0.83% w/v solids beads containing $1.39 \times 10^1$ particles removed $1.79 \times 10_7$ platelets, yielding a particle-to-platelet ratio of 779.

EXAMPLE 6.

Magnetic Bead Depletion of White Blood Cells.

The preparation of leuko-rich samples, their depletion with KC-56 monoclonal antibody (Coulter Corporation) conjugated, 5X-aminodextran coated manganese ferrite particles and the analysis of the supernatant liquids after magnetic depletion according to Procedure 1 are similar to those described for neutrophil depletion using 1D3 antibody-conjugated magnetic beads. The depletion assay was conducted using 5, 10, 20, 40, 60, 80, 100, 150, 200 and 250 µL of 0.833% w/v solids, KC-56 conjugated, 5X-aminodextran coated manganese ferrite particles. The llymphocyte, monocyte and granulocyte counts for the undepleted control sample, given as fluorescent events, are listed in the following depletion Table 8 as 0 µL beads.

TABLE 8

| µL Beads | Counts lymphocytes | monocytes | granulocytes |
|---|---|---|---|
| 0 | 25,461 | 11,730 | 40,740 |
| 5 | 15,660 | 6,447 | 53,165 |
| 10 | 13,746 | 5,801 | 60,708 |
| 20 | 3,474 | 3,589 | 50,268 |
| 40 | 1,266 | 1,362 | 30,370 |
| 60 | 251 | 123 | 6,147 |
| 80 | 100 | 83 | 4,333 |
| 100 | 89 | 5 | 201 |
| 150 | 16 | 0 | 8 |
| 200 | 6 | 1 | 4 |
| 250 | 0 | 0 | 1 |

To determine the number of cells per volume of sample, the wbc count ($2.86 \times 10^6$) of the undepleted sample was determined for a 100 µL aspiration on a Coulter S-Plus® counter and this count compared with the total fluorescent events ($8.57 \times 10^5$) for lymphocytes, monocytes and granulocytes in an undepleted sample and 100 µL aspiration on the Coulter EPICS® Profile II flow cytometer. As a result, the fluorescent events were scaled by a factor of 3.34 [that is, $(2.86 \times 10^6) \div (8.57 \times 10^5)$] and the dilution factor of 11 to obtain cell numbers. Bead numbers were calculated using $1.39 \times 10^{11}$ particles/ml for a 0.833% w/v solids suspension. The following depletion Table 9 tabulates the results as number of wbc depleted $\times 10^5$, number of magnetic beads using in the depletion $\times 10^8$ and the bead-to-cell ratio $\times 10^3$.

TABLE 9

| µL Beads | WBC × 10⁵ Depleted | No. Beads × 10⁸ Used in Depletion | Bead-to-Cell Ratio × 10³ |
|---|---|---|---|
| 0 | | | |
| 5 | 5.54 | 6.97 | 1.26 |
| 10 | 6.48 | 13.9 | 2.15 |
| 20 | 11.1 | 27.9 | 2.52 |
| 40 | 16.5 | 55.8 | 3.38 |
| 60 | 26.2 | 83.6 | 3.19 |
| 80 | 27.0 | 111 | 4.13 |
| 100 | 28.5 | 139 | 4.89 |
| 150 | 28.6 | 209 | 7.30 |
| 200 | 28.3 | 279 | 9.74 |
| 250 | 28.6 | 348 | 12.2 |

Figure 5:
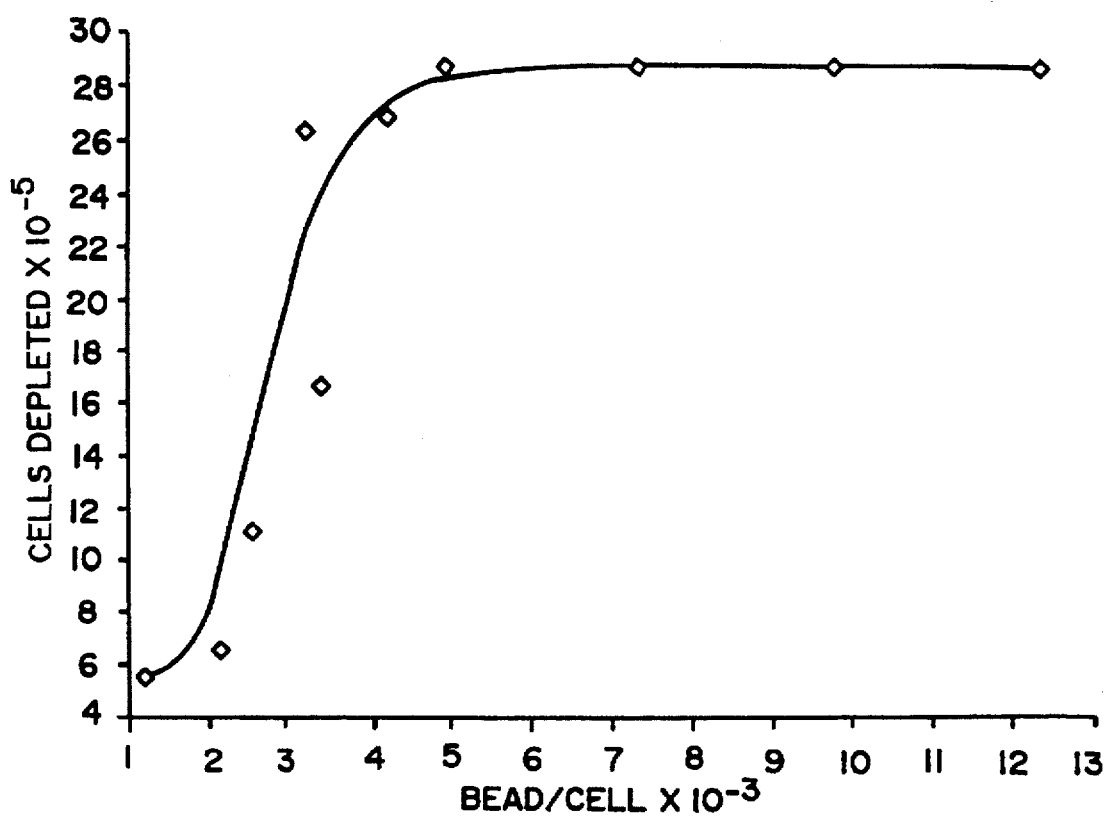
FIG. 5 is a plot of the number of white blood cells depleted versus the magnetic bead-to-cell ratio.

FIG. 5 is a plot of the number of wbcs depleted versus the magnetic bead-to-cell ratio. FIG. 5 shows a steep rise for the bead-to-cell values of $2.15 \times 10^3$ and $4.13 \times 10^3$, and a plateau starting at 100 µL of 0.833% w/v bead titer where $2.85 \times 10^6$ wbcs were depleted at a bead-to-cell ratio of about 4900:1. The removal of the larger granulocytes cells begins after almost all of the llymphocytes and monocytes were depleted. This is consistent with the requirement of needing a greater number of magnetic beads attached to a granulocyte to magnetically remove these cells. That is, for magnetic separation of granulocytes it is necessary to have more magnetic particles attached to each of the larger granulocyte cells in order to have sufficient magnetic moment to physically pull the cells from solution toward the magnetic field. There is no separate inflection point shown in FIG. 5 for granulocyte depletion. However, some granulocytes were shafted in the forward versus side scatter histograms for higher titers and Just prior to complete depletion. This indicates the presence of some granulocytes that were not removed by magnetic separation, but remained in suspension with significant numbers of magnetic beads attached to the cells.

We claim:

1. A method of preparing aminodextran compounds in aqueous solution comprising:

(a) partially oxidizing a dextran compound to dextran aldehyde using a chemical oxidizing agent such as sodium periodate at ambient room temperature;

(b) desalting the dextran-aldehyde solution of step (a);

(c) reacting the dextran-aldehyde of step (b) with a diamine at a temperature of about 5–10° C. to form a plurality of Schiff's base linkages between the dextran-aldehyde and amino groups of the diamine; and (d) reducing the Schiff's base linkages of step (c) to obtain an amino-dextran through the use of a chemical reducing agent.

2. The method of claim 1 wherein said dextran has a molecular weight in the range of 10,000 to two million daltons.

3. The method of claim 1 wherein said diamine is 1,3-diaminopropane.

4. The method of claim 1 wherein the diamine to periodate used has a molar ratio of greater than 2.2:1.

5. The method of claim 1 wherein the diamine to chemical oxidizing agent used has a molar ratio of about 2.2:1.

6. The aminodextran compounds produced by the method of claim 1.

7. The aminodextran compounds produced by the method of claim 1 wherein said compounds have a degree of sugar substitution in the range of about 3.3% to about 16.5%.

8. A method of preparing aminodextran compounds having about 3.3% to about 16.5% of sugar residues doubly-substituted by diamine groups, said method comprising:

(a) adding an aqueous periodate solution to an aqueous dextran solution over about a ten minute time period with vigorous stirring during the addition and stemming the resulting reaction mixture at room temperature for about 1.5 to about 3 hours to obtain a mixture wherein the dextran is partially oxidized to dextran aldehyde;

(b) desalting and washing the mixture of step (a) to obtain a solution of the polymer dextran-aldehyde;

(c) cooling the solution of polymer of step (b) to a temperature of about 5–10° C., adding a diamine to the cooled solution over about a ten minute time period and reacting the resulting mixture for a sufficient time to form Schiff's base, the duration of the reaction being determined by spectroscopic monitoring of the Schiff's base formation and the molar amount of diamine added to the reaction mixture being greater than 2.2 times the molar amount of periodate used in step (a);

(d) reducing the Schiff's base by reaction with borohydride anion in aqueous hydroxide at room temperature, the duration of said reaction being determined by spectroscopically monitoring the disappearance of the Schiff's base to yield a reduced aminodextran; and (e) purifying and drying the polymeric product of step (d) to obtain said aminodextran.

9. The method of claim 8 wherein said dextran has a molecular weight in the range of about 10,000 to two million Daltons.

10. The method of claim 8 wherein the diamine and periodate are used in a molar ratio of about 2.2:1.

11. The method of claim 8 wherein said diamine is 1,3-diaminopropane.

12. The method of claim 8 wherein said temperature is in the range of 5–10° C.

13. The method of claim 8 wherein the product of step (d) is purified by dialysis or hollow fiber membrane filtration to optimize yield.

* * * * *